(12) United States Patent
Yoshida et al.

(10) Patent No.: US 7,439,006 B2
(45) Date of Patent: Oct. 21, 2008

(54) SALT SUITABLE FOR AN ACID GENERATOR AND A CHEMICALLY AMPLIFIED POSITIVE RESIST COMPOSITION CONTAINING THE SAME

(75) Inventors: Isao Yoshida, Ikeda (JP); Yukako Harada, Settsu (JP); Takayuki Miyagawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/889,353

(22) Filed: Aug. 10, 2007

(65) Prior Publication Data

US 2008/0076063 A1 Mar. 27, 2008

(30) Foreign Application Priority Data

Aug. 18, 2006 (JP) .............................. 2006-223039

(51) Int. Cl.
*G03F 7/004* (2006.01)
*C07C 69/00* (2006.01)

(52) U.S. Cl. .................. 430/270.1; 430/921; 560/129; 560/150

(58) Field of Classification Search .............. 430/270.1, 430/921; 560/1, 129, 150
See application file for complete search history.

(56) References Cited

U.S. PATENT DOCUMENTS

| | | | |
|---|---|---|---|
| 6,383,713 B1 | 5/2002 | Uetani et al. | |
| 6,548,221 B2 | 4/2003 | Uetani et al. | |
| 6,908,722 B2 * | 6/2005 | Ebata et al. | ............. 430/270.1 |
| 7,262,321 B2 * | 8/2007 | Harada et al. | ............. 560/129 |
| 7,301,047 B2 * | 11/2007 | Yoshida et al. | ............. 560/129 |
| 7,304,175 B2 * | 12/2007 | Harada et al. | ............. 560/129 |
| 2003/0194639 A1 | 10/2003 | Miya et al. | |
| 2007/0122750 A1 * | 5/2007 | Yamaguchi et al. | ......... 430/311 |

OTHER PUBLICATIONS

U.S. Appl. No. 11/353,010, filed Feb. 14, 2006.
U.S. Appl. No. 11/390,319, filed Mar. 28, 2006.
U.S. Appl. No. 11/390,365, filed Mar. 28, 2006.
U.S. Appl. No. 11/586,640, filed Oct. 26, 2006.
U.S. Appl. No. 11/586,638, filed Oct. 26, 2006.
U.S. Appl. No. 11/516,644, filed Sep. 7, 2006.
U.S. Appl. No. 11/600,884, filed Nov. 17, 2006.
U.S. Appl. No. 11/644,955, filed Dec. 26, 2006.

* cited by examiner

*Primary Examiner*—John S Chu
(74) *Attorney, Agent, or Firm*—Birch, Stewart, Kolasch & Birch, LLP

(57) ABSTRACT

A salt represented by the formula (I):

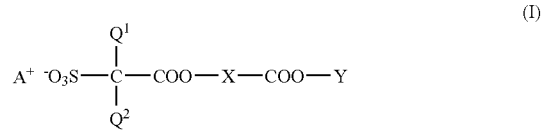

wherein X represents a C1-C12 divalent linear or branched chain hydrocarbon group, Y represents a C1-C30 hydrocarbon group which may be substituted with at least one substituent, and at least one —$CH_2$— in the C1-C30 hydrocarbon group may be substituted with —O— or —CO—, $Q^1$ and $Q^2$ each independently represent a fluorine atom or a C1-C6 perfluoroalkyl group, and $A^+$ represents an organic counter ion.

The present invention further provides a chemically amplified resist composition comprising the salt represented by the above-mentioned formula (I).

21 Claims, No Drawings

SALT SUITABLE FOR AN ACID GENERATOR AND A CHEMICALLY AMPLIFIED POSITIVE RESIST COMPOSITION CONTAINING THE SAME

This nonprovisional application claims priority under 35 U.S.C. § 119(a) on Patent Application No. 2006-223039 filed in JAPAN on Aug. 18, 2006, the entire contents of which are hereby incorporated by reference.

FIELD OF THE INVENTION

The present invention relates to a salt suitable for an acid generator used for a chemically amplified resist composition which is used in fine processing of semiconductors, and a chemically amplified positive resist composition containing the same.

BACKGROUND OF THE INVENTION

A chemically amplified positive resist composition used for semiconductor microfabrication employing a lithography process contains an acid generator comprising a compound generating an acid by irradiation.

In semiconductor microfabrication, it is desirable to form patterns having high resolution and excellent exposure margin, and it is expected for a chemically amplified resist composition to give such patterns.

U.S. Pat. No. 6,548,221 B2 and U.S. Pat. No. 6,383,713 B1 disclose a chemically amplified resist composition containing triphenylsulfonium perfluorobutanesulfonate as the acid generator.

US 2003/0194639 A1 also discloses a chemically amplified resist composition containing the salt represented by the following formulae:

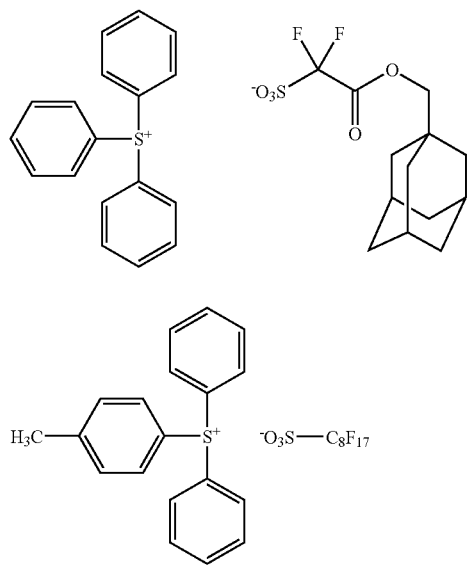

or the like as the acid generator.

SUMMARY OF THE INVENTION

An object of the present invention is to provide a salt suitable for an acid generator capable of providing a chemically amplified resist composition giving patterns having high resolution and excellent exposure margin.

Other objects of the present invention are to provide a synthetic intermediate for the salt and to provide a process for producing the synthetic intermediate or the salt.

Still another object of the present invention is to provide a chemically amplified resist composition containing the salt.

These and other objects of the present invention will be apparent from the following description.

The present invention relates to the followings:

<1> A salt represented by the formula (I):

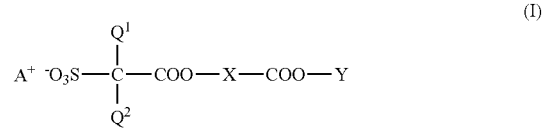

wherein X represents a C1-C12 divalent linear or branched chain hydrocarbon group, Y represents a C1-C30 hydrocarbon group which may be substituted with at least one substituent, and at least one $—CH_2—$ in the C1-C30 hydrocarbon group may be substituted with $—O—$ or $—CO—$, $Q^1$ and $Q^2$ each independently represent a fluorine atom or a C1-C6 perfluoroalkyl group, and $A^+$ represents an organic counter ion;

<2> The salt according to <1>, wherein $Q^1$ and $Q^2$ each independently represent a fluorine atom or a trifluoromethyl group;

<3> The salt according to <1> or <2>, wherein the organic counter ion is at least one cation selected from a cation represented by the formula (IIa):

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

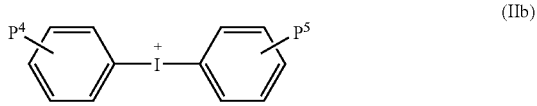

wherein $P^4$ and $P^5$ each independently represent a hydrogen atom, a hydroxyl group, a C1-C12 alkyl group or a C1-C12 alkoxy group, a cation represented by the formula (IIc):

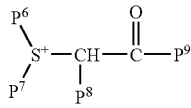 (IIc)

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —$CH_2$— in the divalent acyclic hydrocarbon group may be substituted with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ are bonded to form a divalent acyclic hydrocarbon group which forms a 2-oxocycloalkyl group together with the adjacent —CHCO—, and at least one —$CH_2$— in the divalent acyclic hydrocarbon group may be substituted with —CO—, —O— or —S—, and a cation represented by the formula (IId):

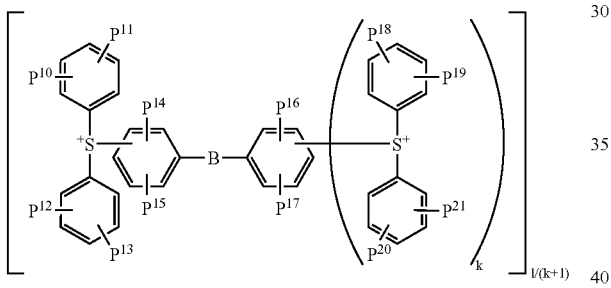 (IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1;

<4> The salt according to <1> or <2>, wherein the organic counter ion is a cation represented by the formula (IIIa), (IIIb) or (IIIc):

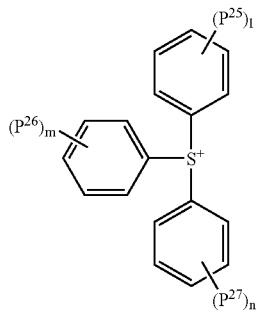 (IIIa)

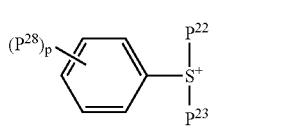 (IIIb)

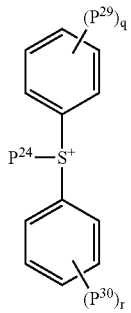 (IIIc)

wherein $P^{22}$, $P^{23}$ and $P^{24}$ each independently represent a C1-C20 alkyl group or a C3-C30 cyclic hydrocarbon group except a phenyl group, wherein at least one hydrogen atom in the C1-C20 alkyl group may be substituted with a hydroxyl group, a C1-C12 alkoxy group or a C3-C12 cyclic hydrocarbon group and where in at least one hydrogen atom in the C3-C30 cyclic hydrocarbon group may be substituted with a hydroxyl group, a C1-C12 alkyl group or a C1-C12 alkoxy group, and $P^{25}$, $P^{26}$, $P^{27}$, $P^{28}$, $P^{29}$ and $P^{30}$ each independently represent a hydroxyl group, a C1-C12 alkyl group, a C1-C12 alkoxy group or a C3-C12 cyclic hydrocarbon group, and l, m, n, p, q and r each independently represent an integer of 0 to 5;

<5> The salt according to <1> or <2>, wherein the organic counter ion is a cation represented by the formula (IIIa):

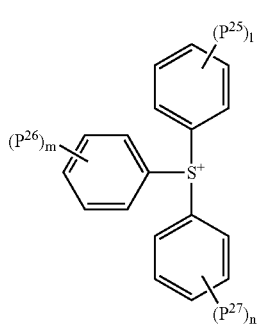 (IIIa)

wherein $P^{25}$, $P^{26}$, $P^{27}$, l, m and n are the same meanings as defined in above-mentioned <4>;

<6> The salt according to any one of <1> to <5>, wherein Y represents a C1-C20 hydrocarbon group which may be substituted with at least one selected from a C1-C6 alkoxy group, a C1-C4 perfluoroalkyl group, a C1-C6 hydroxyalkyl group, a hydroxyl group and a cyano group, and at least one —$CH_2$— except terminal —$CH_2$— in the C1-C20 hydrocarbon group may be substituted with —O— or —CO—;

<7> The salt according to any one of <1> to <6>, wherein the C1-C12 divalent linear or branched chain hydrocarbon group is a following group;

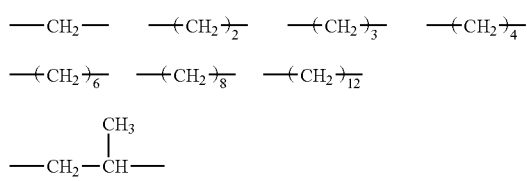

<8> The salt according to any one of <1> to <6>, wherein the C1-C12 divalent linear or branched chain hydrocarbon group is a methylene, ethylene, trimethylene, tetramethylene, hexamethylene, octamethylene or dodecamethylene group;

<9> The salt according to <1>, wherein the salt represented by the formula (I) is one represented by the formula (IVa), (IVb) or (IVc):

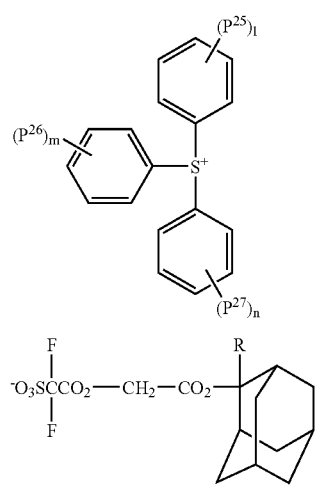 (IVa)

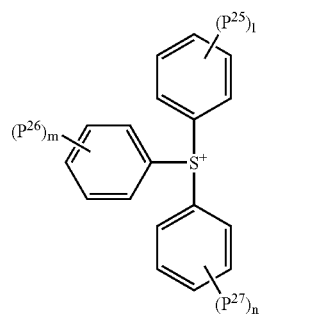 (IVb)

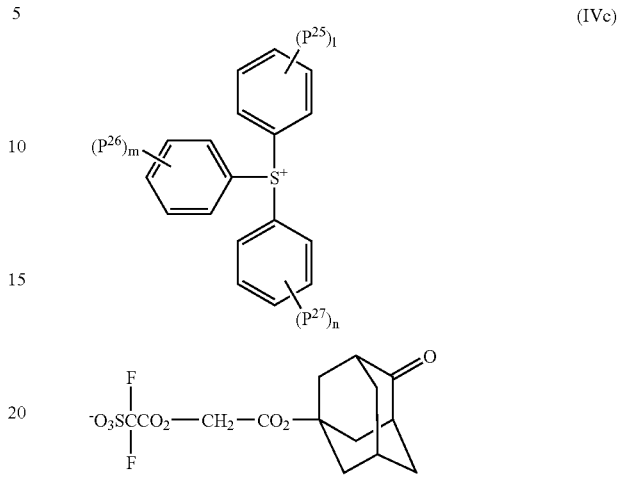 (IVc)

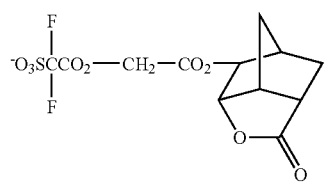

wherein $P^{25}$, $P^{26}$, $P^{27}$, l, m and n are the same meanings as defined in above-mentioned <4> and R represents a C1-C6 alkyl group;

<10> A salt represented by the formula (V):

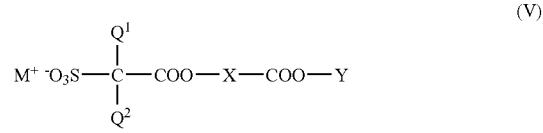 (V)

wherein X represents a C1-C12 divalent linear or branched chain hydrocarbon group, Y represents a C1-C30 hydrocarbon group which may be substituted with at least one substituent, and at least one —$CH_2$— in the C1-C30 hydrocarbon group may be substituted with —O— or —CO—, $Q^1$ and $Q^2$ each independently represent a fluorine atom or a C1-C6 perfluoroalkyl group, and M represents Li, Na, K or Ag;

<11> A process for production of a salt represented by the formula (V):

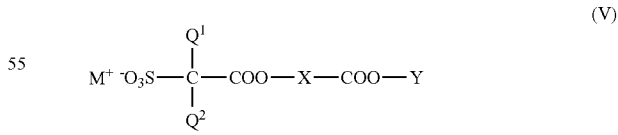 (V)

wherein X represents a C1-C12 divalent linear or branched chain hydrocarbon group, Y represents a C1-C30 hydrocarbon group which may be substituted with at least one substituent, and at least one —$CH_2$— in the C1-C30 hydrocarbon group may be substituted with —O— or —CO—, $Q^1$ and $Q^2$ each independently represent a fluorine atom or a C1-C6 perfluoroalkyl group, and M represents Li, Na, K or Ag, which comprises reacting a compound represented by the formula (VI):

Z-X—COO—Y (VI)

wherein X and Y are the same as defined above, and Z represents Cl, Br or I, with a compound represented by the formula (VII):

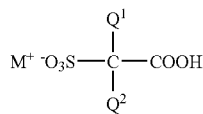

(VII)

$$M^+ \ ^-O_3S-\underset{Q^2}{\overset{Q^1}{C}}-COOH$$

wherein $Q^1$, $Q^2$ and M are the same as defined above;

<12> A process for production of a salt represented by the formula (I):

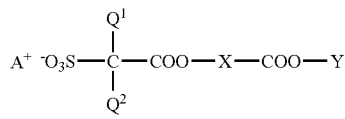

(I)

$$A^+ \ ^-O_3S-\underset{Q^2}{\overset{Q^1}{C}}-COO-X-COO-Y$$

wherein X represents a C1-C12 divalent linear or branched chain hydrocarbon group, Y represents a C1-C30 hydrocarbon group which may be substituted with at least one substituent, and at least one —CH$_2$— in the C1-C30 hydrocarbon group may be substituted with —O— or —CO—, $Q^1$ and $Q^2$ each independently represent a fluorine atom or a C1-C6 perfluoroalkyl group, and A$^+$ represents an organic counter ion, which comprises reacting a salt represented by the formula (V):

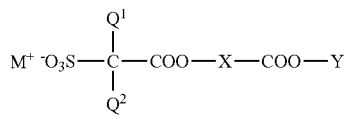

(V)

$$M^+ \ ^-O_3S-\underset{Q^2}{\overset{Q^1}{C}}-COO-X-COO-Y$$

wherein X, Y, $Q^1$ and $Q^2$ are the same as defined above and M represents Li, Na, K or Ag, with a compound represented by the formula (VIII):

A$^+$—L (VIII)

wherein A$^+$ is as defined above and L represents F, Cl, Br, I, BF$_4$, AsF$_6$, SbF$_6$, PF$_6$ or ClO$_4$;

<13> A process for production of a salt represented by the formula (I):

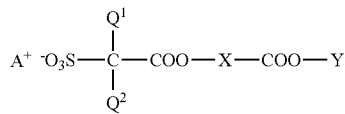

(I)

$$A^+ \ ^-O_3S-\underset{Q^2}{\overset{Q^1}{C}}-COO-X-COO-Y$$

wherein X represents a C1-C12 divalent linear or branched chain hydrocarbon group, Y represents a C1-C30 hydrocarbon group which may be substituted with at least one substituent, and at least one —CH$_2$— in the C1-C30 hydrocarbon group may be substituted with —O— or —CO—, $Q^1$ and $Q^2$ each independently represent a fluorine atom or a C1-C6 perfluoroalkyl group, and A$^+$ represents an organic counter ion, which comprises reacting a salt represented by the formula (IX):

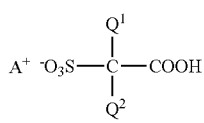

(IX)

$$A^+ \ ^-O_3S-\underset{Q^2}{\overset{Q^1}{C}}-COOH$$

wherein $Q^1$, $Q^2$ and A$^+$ are the same as defined above, with a compound represented by the formula (VI):

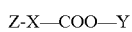

Z-X—COO—Y (VI)

wherein X and Y are the same as defined above, and Z represents Cl, Br or I;

<14> A chemically amplified positive resist composition comprising a salt represented by the formula (I):

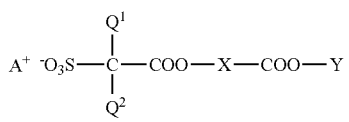

(I)

$$A^+ \ ^-O_3S-\underset{Q^2}{\overset{Q^1}{C}}-COO-X-COO-Y$$

wherein X represents a C1-C12 divalent linear or branched chain hydrocarbon group, Y represents a C1-C30 hydrocarbon group which may be substituted with at least one substituent, and at least one —CH$_2$— in the C1-C30 hydrocarbon group may be substituted with —O— or —CO—, $Q^1$ and $Q^2$ each independently represent a fluorine atom or a C1-C6 perfluoroalkyl group, and A$^+$ represents an organic counter ion, and a resin which contains a structural unit which has an acid-labile group and which itself is insoluble or poorly soluble in an aqueous alkali solution but becomes soluble in an aqueous alkali solution by the action of an acid;

<15> The chemically amplified positive resist composition according to <14>, wherein $Q^1$ and $Q^2$ each independently represent a fluorine atom or a trifluoromethyl group;

<16> The chemically amplified positive resist composition according to <14> or <15>, wherein the organic counter ion is at least one cation selected from a cation represented by the formula (IIa):

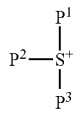

(IIa)

$$P^2-\underset{P^3}{\overset{P^1}{S^+}}$$

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

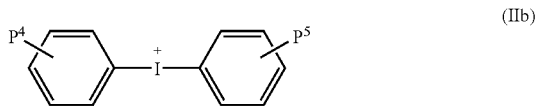

(IIb)

wherein $P^4$ and $P^5$ each independently represent a hydrogen atom, a hydroxyl group, a C1-C12 alkyl group or a C1-C12 alkoxy group, a cation represented by the formula (IIc):

(IIc)

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —$CH_2$— in the divalent acyclic hydrocarbon group may be substituted with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ are bonded to form a divalent acyclic hydrocarbon group which forms a 2-oxocycloalkyl group together with the adjacent —CHCO—, and at least one —$CH_2$— in the divalent acyclic hydrocarbon group may be substituted with —CO—, —O— or —S—, and a cation represented by the formula (IId):

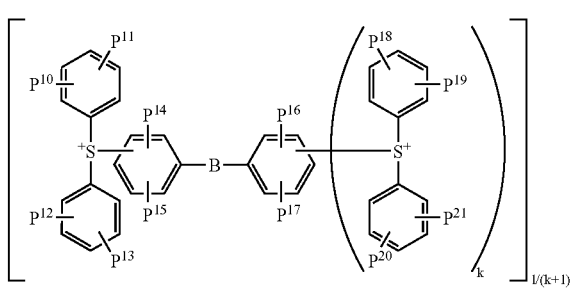

(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1;

<17> The chemically amplified positive resist composition according to <14> or <15>, wherein the organic counter ion is a cation represented by the formula (IIIa), (IIIb) or (IIIc):

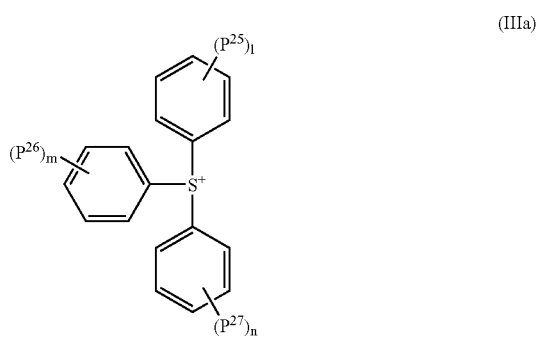

(IIIa)

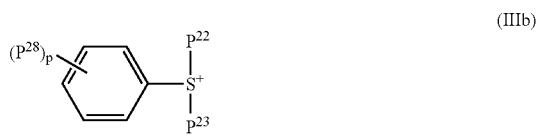

(IIIb)

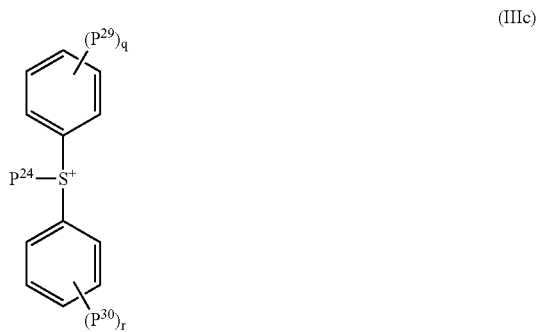

(IIIc)

wherein $P^{22}$, $P^{23}$ and $P^{24}$ each independently represent a C1-C20 alkyl group or a C3-C30 cyclic hydrocarbon group except a phenyl group, wherein at least one hydrogen atom in the C1-C20 alkyl group may be substituted with a hydroxyl group, a C1-C12 alkoxy group or a C3-C12 cyclic hydrocarbon group and wherein at least one hydrogen atom in the C3-C30 cyclic hydrocarbon group may be substituted with a hydroxyl group, a C1-C12 alkyl group or a C1-C12 alkoxy group; and $P^{25}$, $P^{26}$, $P^{27}$, $P^{28}$, $P^{29}$ and $P^{30}$ each independently represent a hydroxyl group, a C1-C12 alkyl group, a C1-C12 alkoxy group or a C3-C12 cyclic hydrocarbon group, and l, m, n, p, q and r each independently represent an integer of 0 to 5;

<18> The chemically amplified positive resist composition according to <14> or <15>, wherein the organic counter ion is a cation represented by the formula (IIIa):

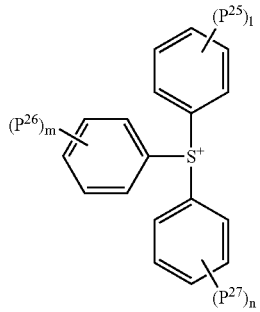
(IIIa)

wherein and $P^{25}$, $P^{26}$, $P^{27}$, l, m and n are the same meanings as defined in above-mentioned <17>;

<19> The chemically amplified positive resist composition according to <14>, wherein the salt represented by the formula (I) is one represented by the formula (IVa), (IVb) or (IVc):

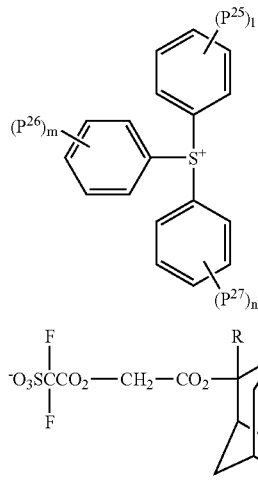
(IVa)

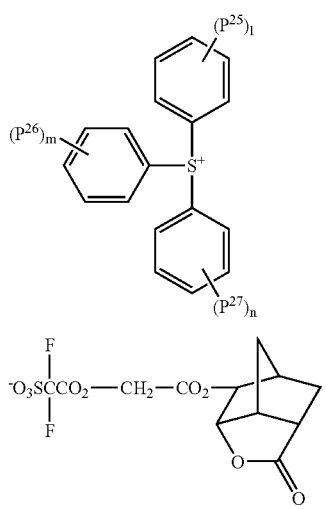
(IVb)

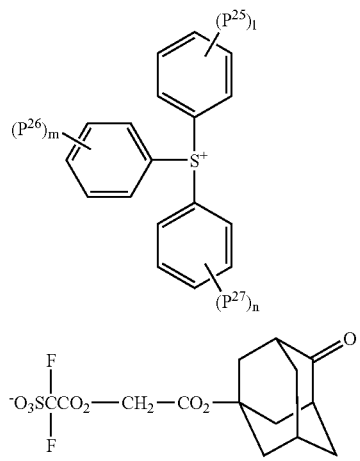
(IVc)

wherein $P^{25}$, $P^{26}$, $P^{27}$, l, m and n are the same meanings as defined in above-mentioned <17> and R represents a C1-C6 alkyl group;

<20> The chemically amplified positive resist composition according to any one of <14> to <19>, the resin contains a structural unit derived from a monomer having a bulky and acid-labile group;

<21> The chemically amplified positive resist composition according to any one of <14> to <19>, wherein the chemically amplified positive resist composition further comprises a basic compound.

DESCRIPTION OF PREFERRED EMBODIMENTS

The present invention provides a salt represented by the formula (I) (hereinafter, simply referred to as Salt (I)).

In Salt (I), X represents a C1-C12 divalent linear or branched chain hydrocarbon group. Examples of the C1-C12 divalent linear or branched chain hydrocarbon group include the followings.

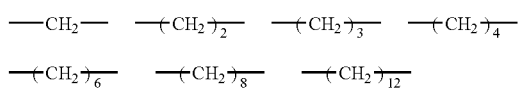

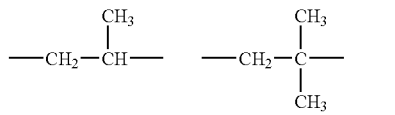

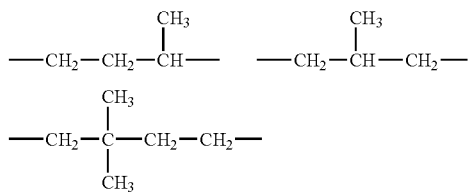

Among them, the following groups:

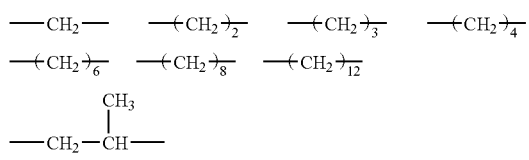

are preferable, and the methylene, ethylene, trimethylene, tetramethylene, hexamethylene, octamethylene and dodecamethylene groups are more preferable, and the methylene, ethylene, trimethylene and tetramethylene groups are especially preferable.

Y represents a C1-C30 hydrocarbon group which may be substituted at least one substituent, and the C1-C20 hydrocarbon group is preferred.

At least one —CH$_2$— in the C1-C30 hydrocarbon group may be substituted with —O— or —CO—.

Examples of the C1-C30 hydrocarbon group include a C1-C30 alkyl group such as a methyl, ethyl, n-propyl, isopropyl, n-butyl, tert-butyl, n-hexyl, n-heptyl, n-octyl, n-decyl, n-undecyl and icosyl group; a C3-C30 cycloalkyl group such as a cyclopentyl, 1-methylcyclopentyl, 1-ethylcyclopentyl, cyclohexyl, 1-methylcyclohexyl, 1-ethylcyclohexyl, 1-n-propylcyclohexyl, norbornyl, 2-methylnorbornyl, 2-ethylnorbornyl, adamantly, 2-methyladamantyl, 2-ethyladamantyl group; a C6-C30 aryl group such as a phenyl, naphthyl, fuluorenyl, anthryl and phenanthryl group; and a C7-C30 aralkyl group such as a benzyl, (2-naphthyl)methyl, 2-(2-naphthyl)ethyl, 2-(1-naphthyl)ethyl, 3-(1-naphthyl)propyl, (9-fluorenyl)methyl, (9-anthryl)methyl and (9-phenanthryl)methyl group.

Examples of the substituent include a hydroxyl group; a cyano group; a C1-C6 alkoxy group such as a methoxy, ethoxy, n-propoxy, isopropoxy, n-butoxy, isobutoxy, tert-butoxy, n-pentyloxy and n-hexyloxy group; a C1-C4 perfluoroalkyl group such as a trifluoromethyl, pentafluoroethyl, heptafluoropropyl and nonafluorobutyl group; a C1-C6 hydroxyalkyl group such as a hydroxymethyl, 2-hydroxyethyl, 3-hydroxypropyl, 4-hydroxybutyl and 6-hydroxyhexyl group.

As the C1-C30 hydrocarbon group, the bulky hydrocarbon groups are preferable.

Specific examples of C1-C30 hydrocarbon group which may be substituted at least one substituent include the followings.

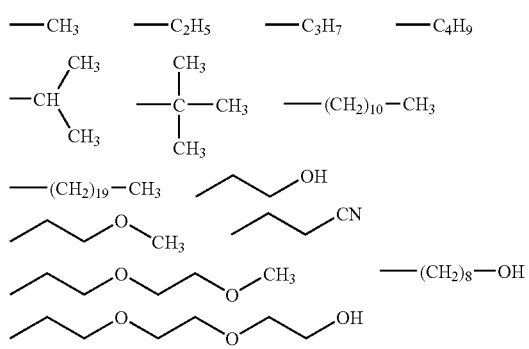

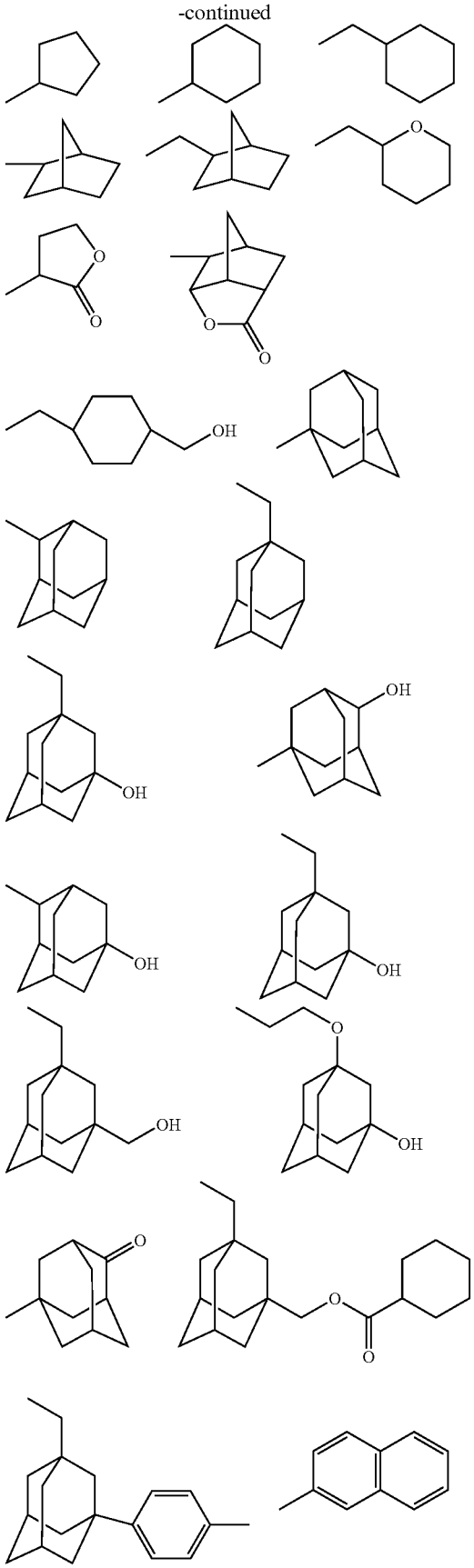

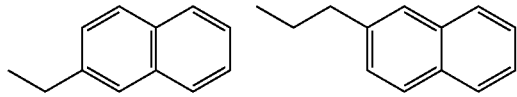
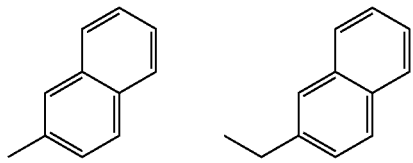
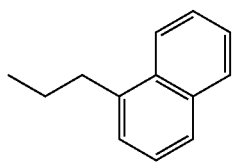
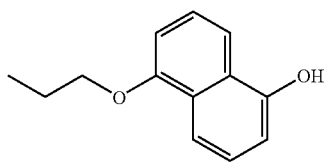
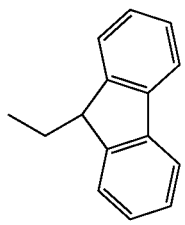
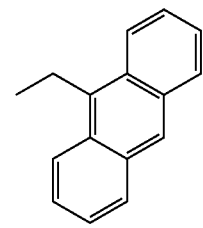
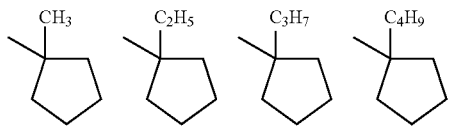
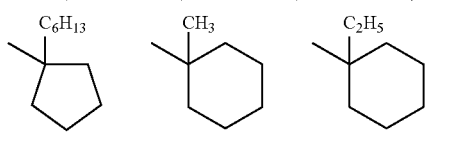
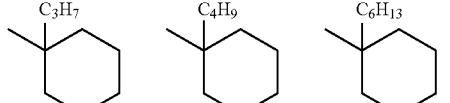
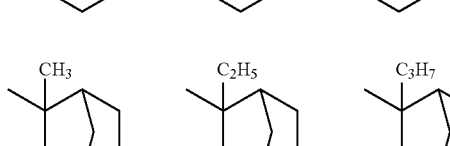
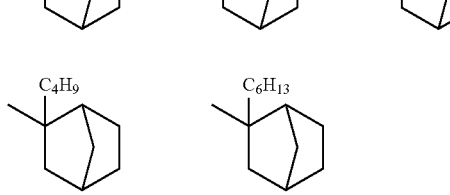
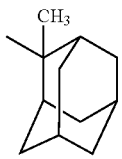 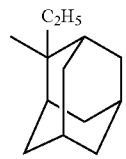 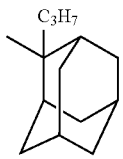
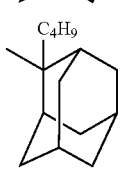 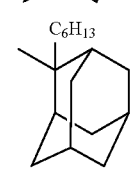
In the above formulae, the straight line with an open end shows a bond extended from an adjacent group.
Among them, the following groups:
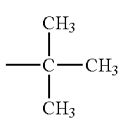 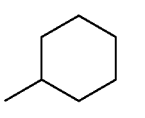 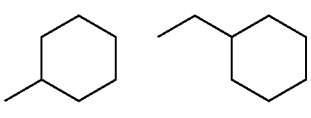
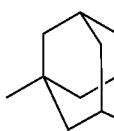 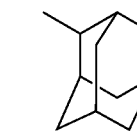 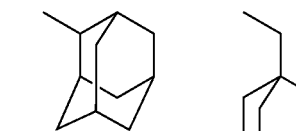
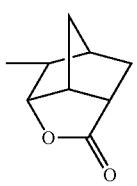 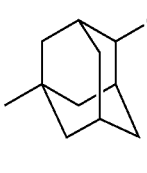 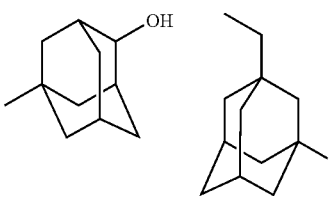
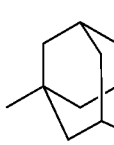 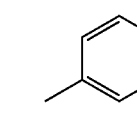 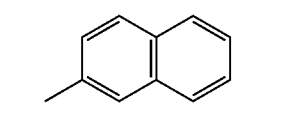
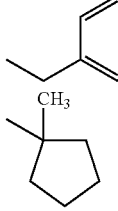 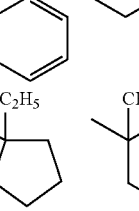 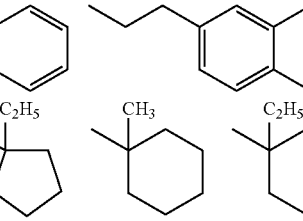

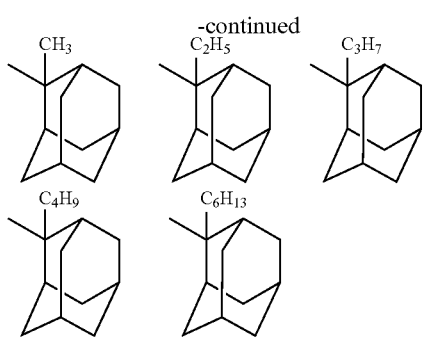

are preferable, the following groups:

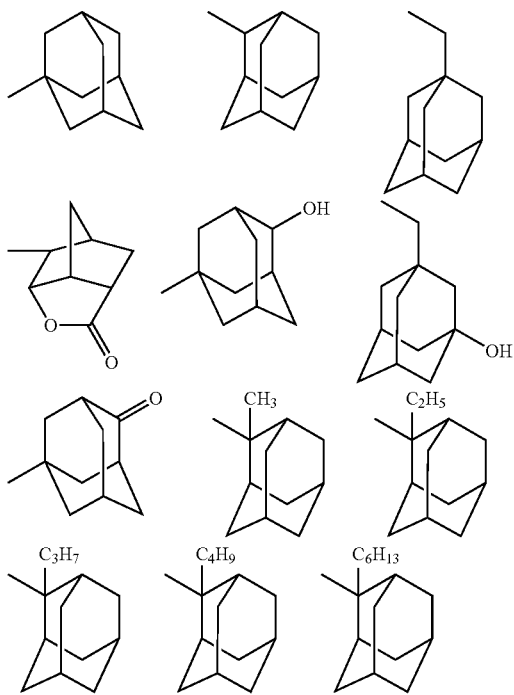

are more preferable, and the followings

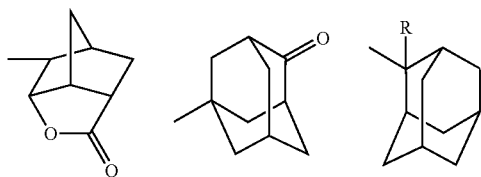

wherein R represents a C1-C6 alkyl group, are especially preferable.

In the above formulae, the straight line with an open end shows a group.

$Q^1$ and $Q^2$ each independently represent a fluorine atom or a C1-C6 perfluoroalkyl group.

Examples of the C1-C6 perfluoroalkyl group include a trifluoromethyl, pentafluoroethyl, heptafluoropropyl, nonafluorobutyl undecafluoropentyl and tridecafluorohexyl group, and the trifluoromethyl group is preferable.

It is preferred that $Q^1$ and $Q^2$ each independently represent the fluorine atom or the trifluoromethyl group, and it is more preferred that $Q^1$ and $Q^2$ represent the fluorine atoms.

Specific examples of the anion part of Salt (I) include the following:

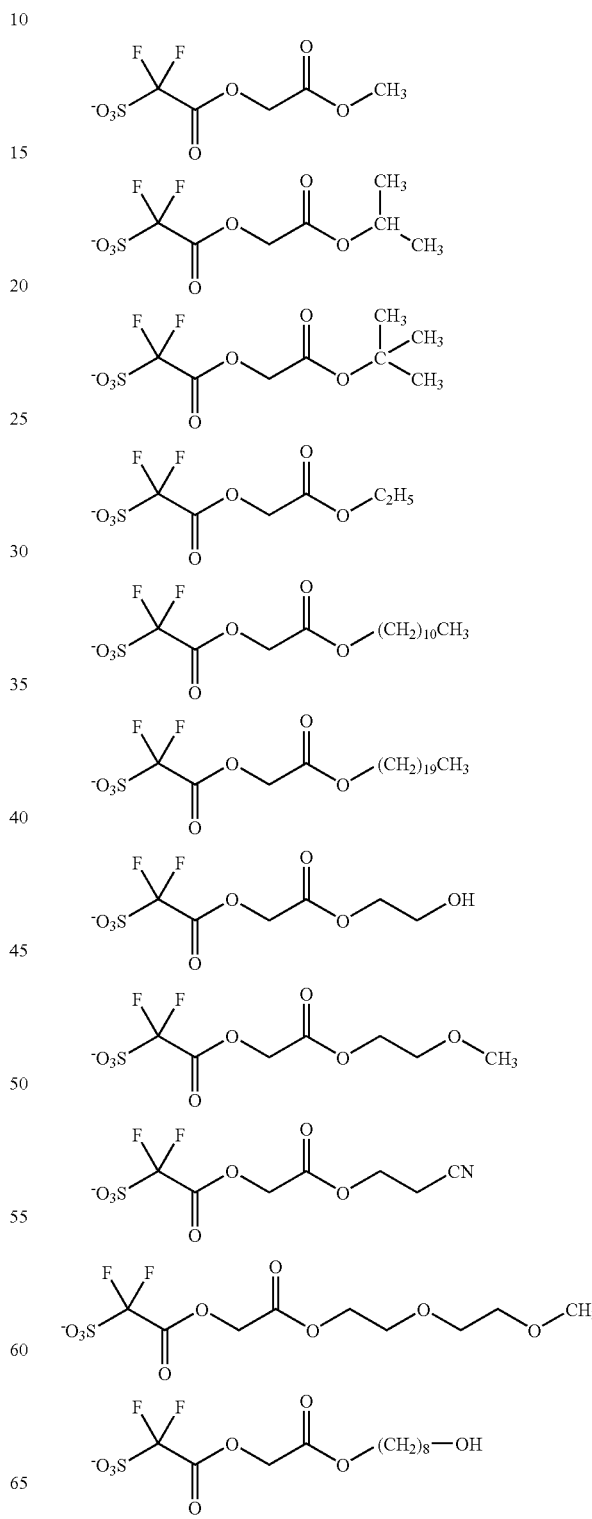

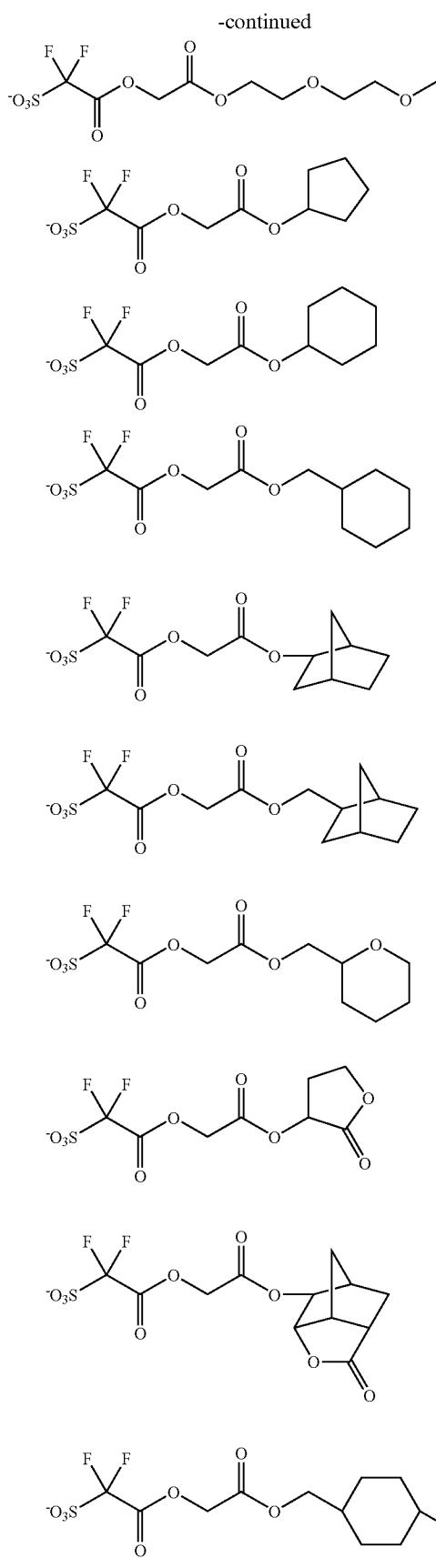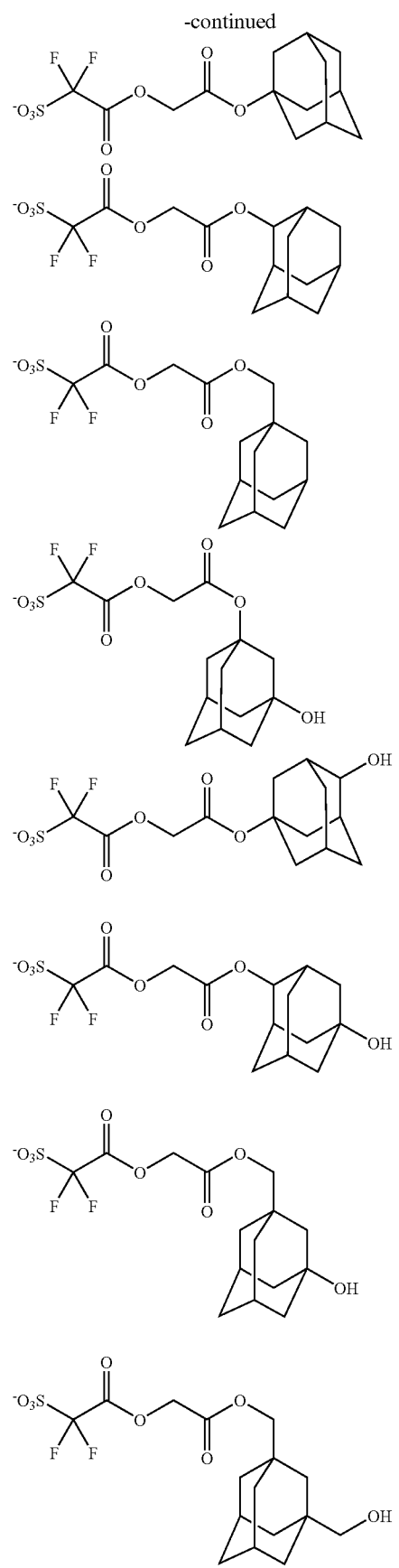

-continued
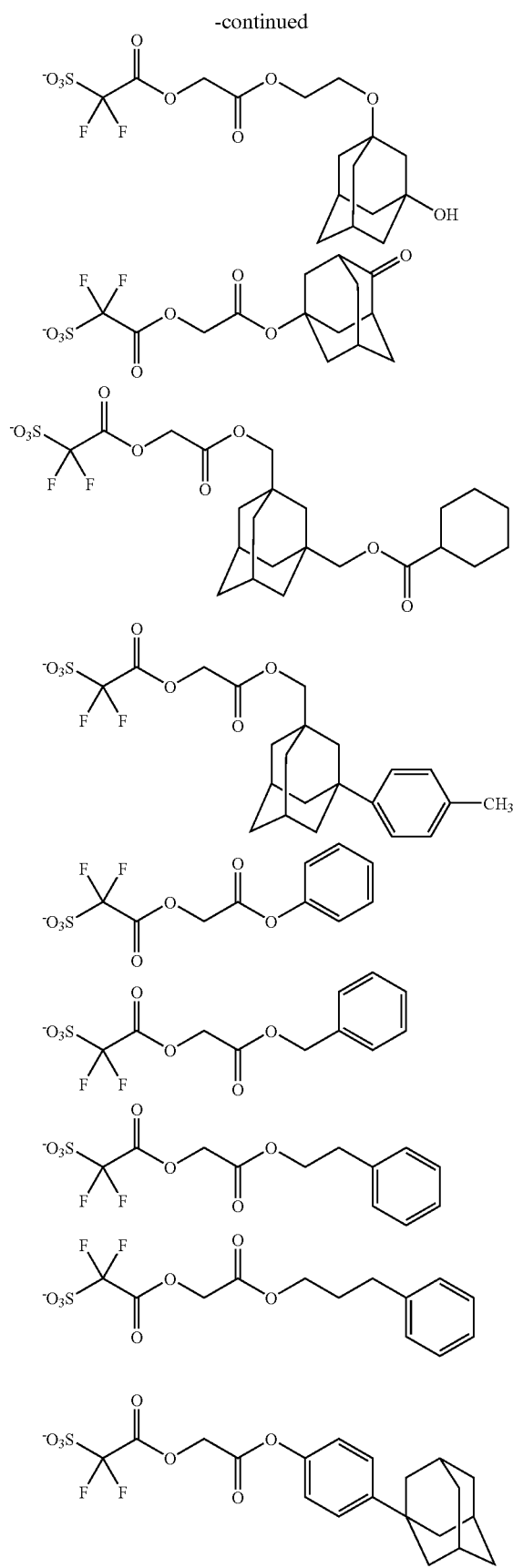
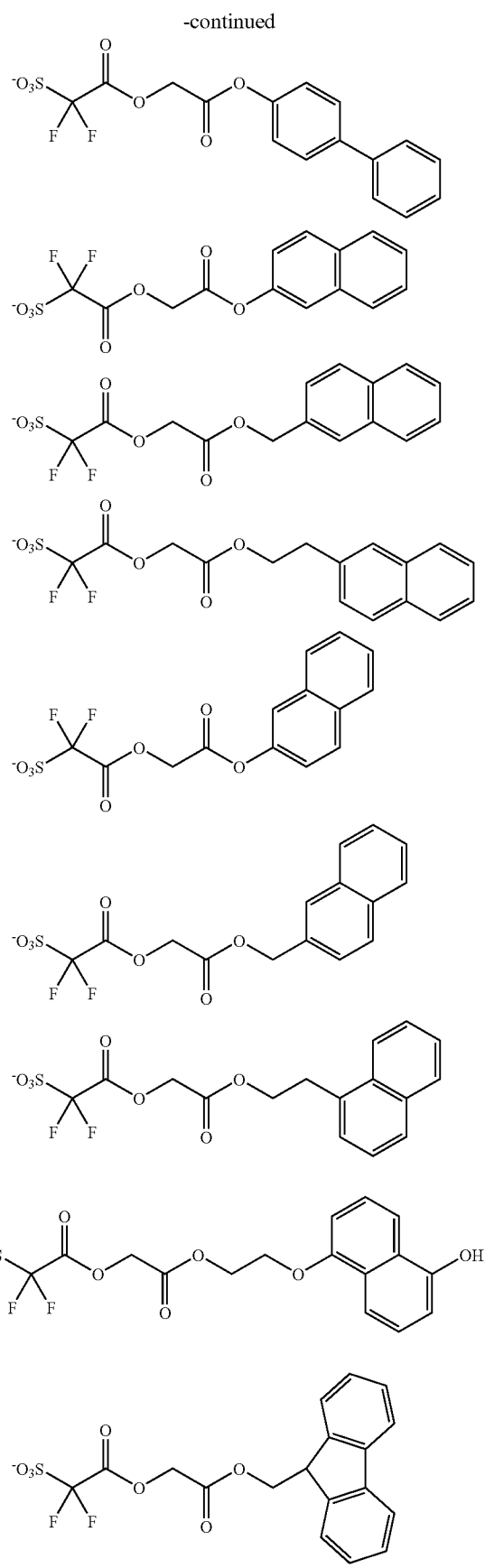

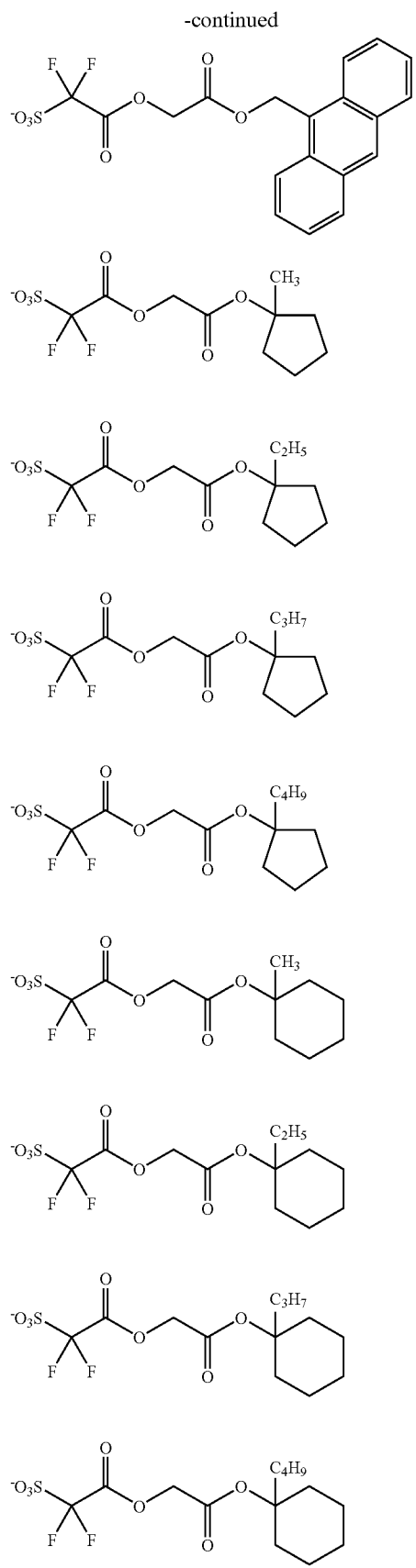
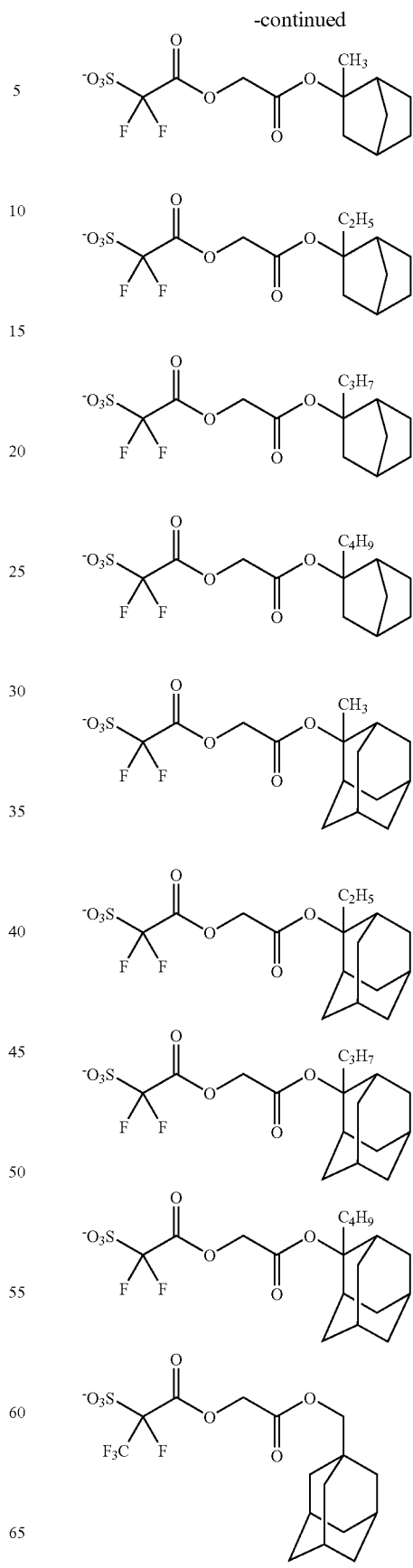

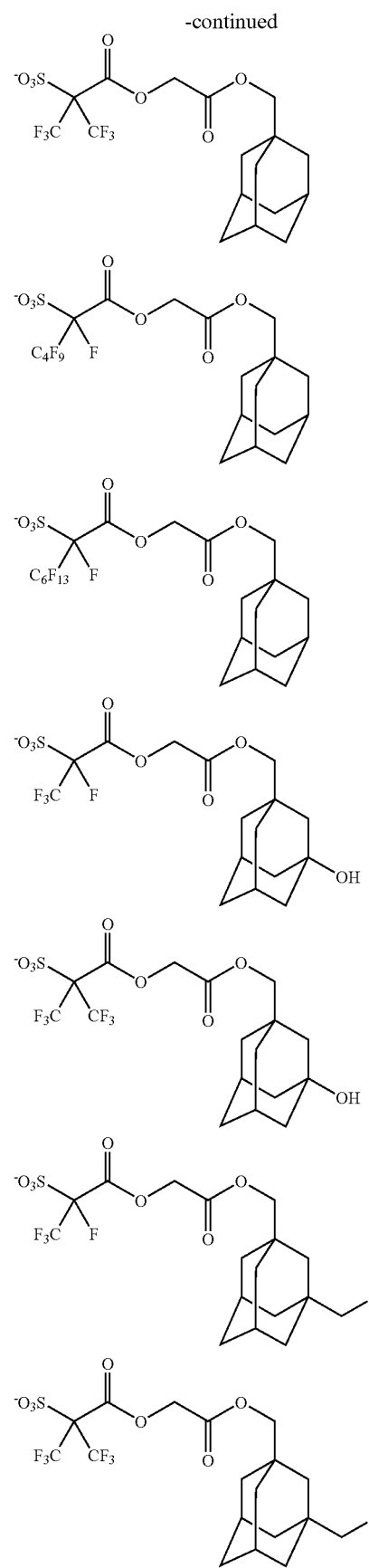
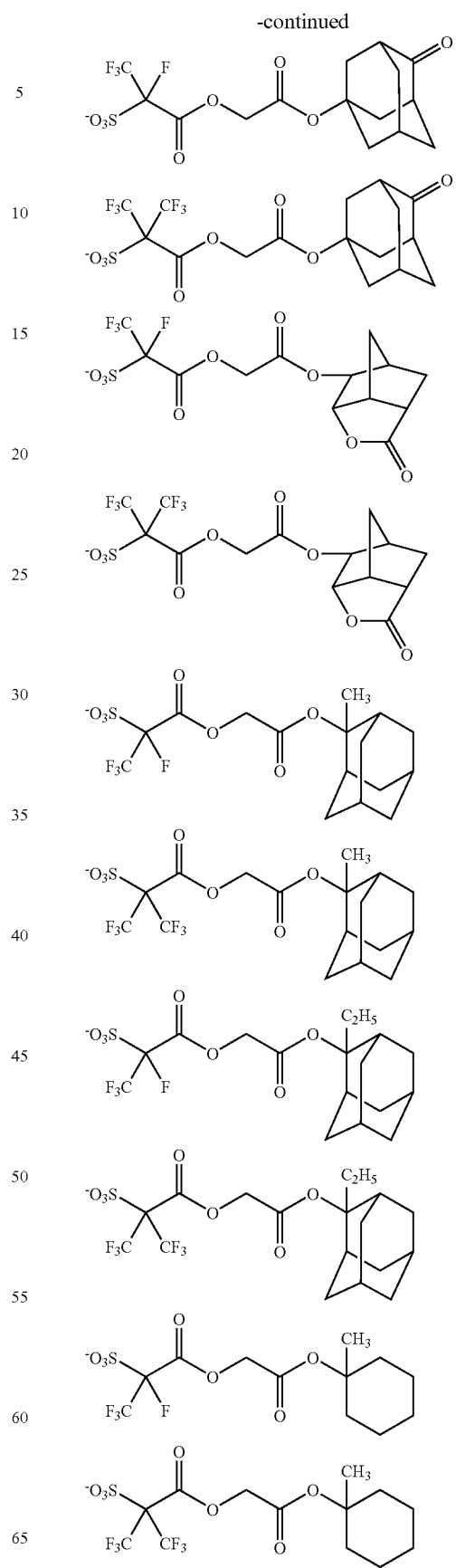

-continued
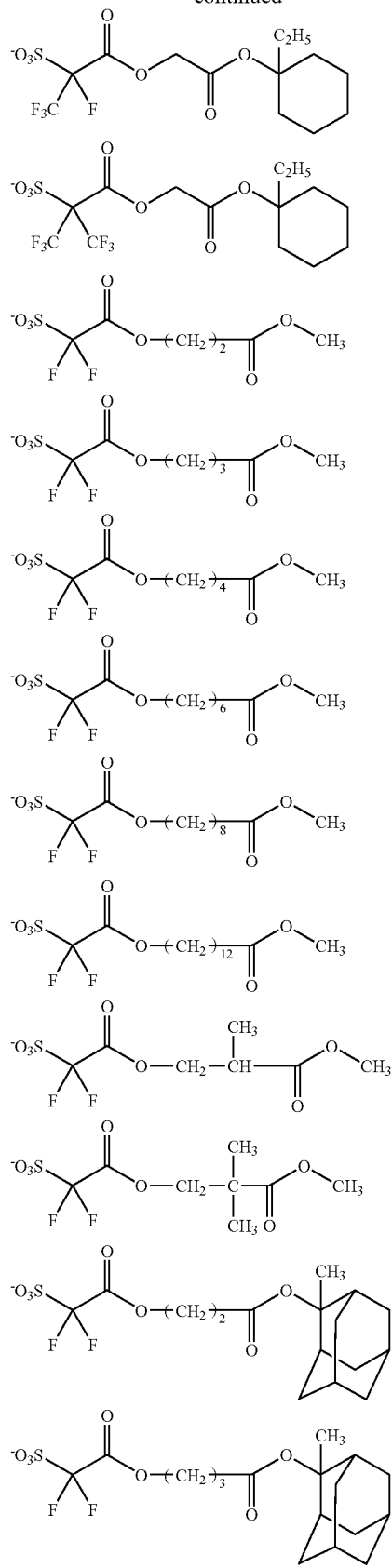
-continued
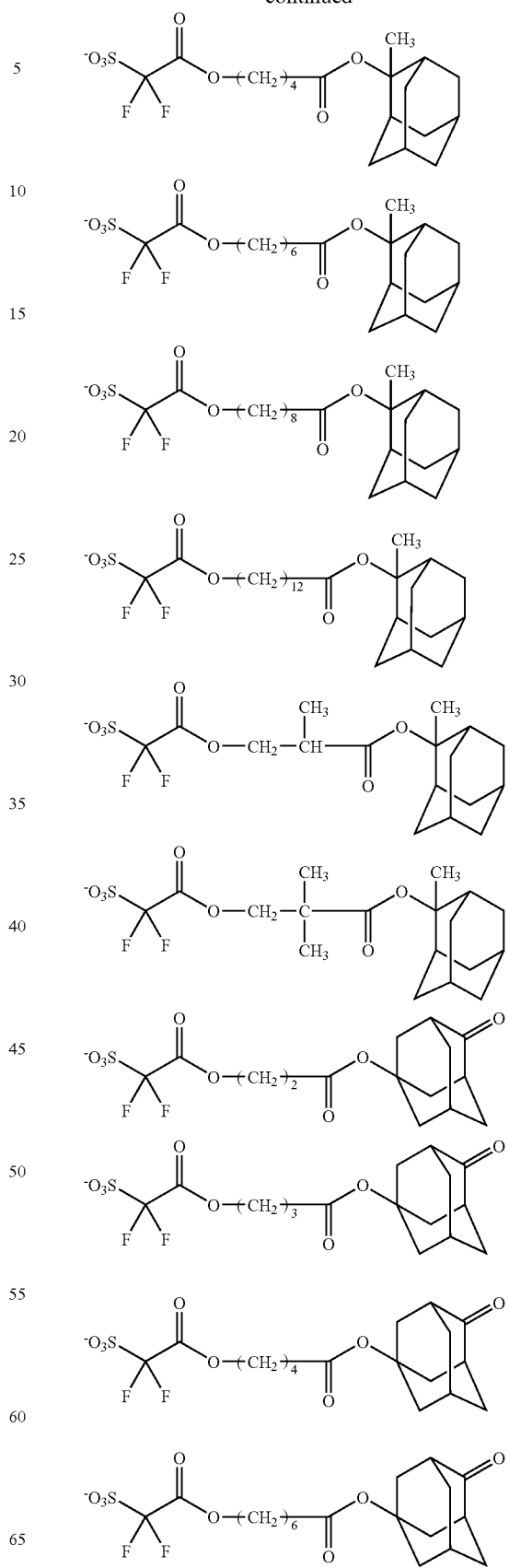

-continued
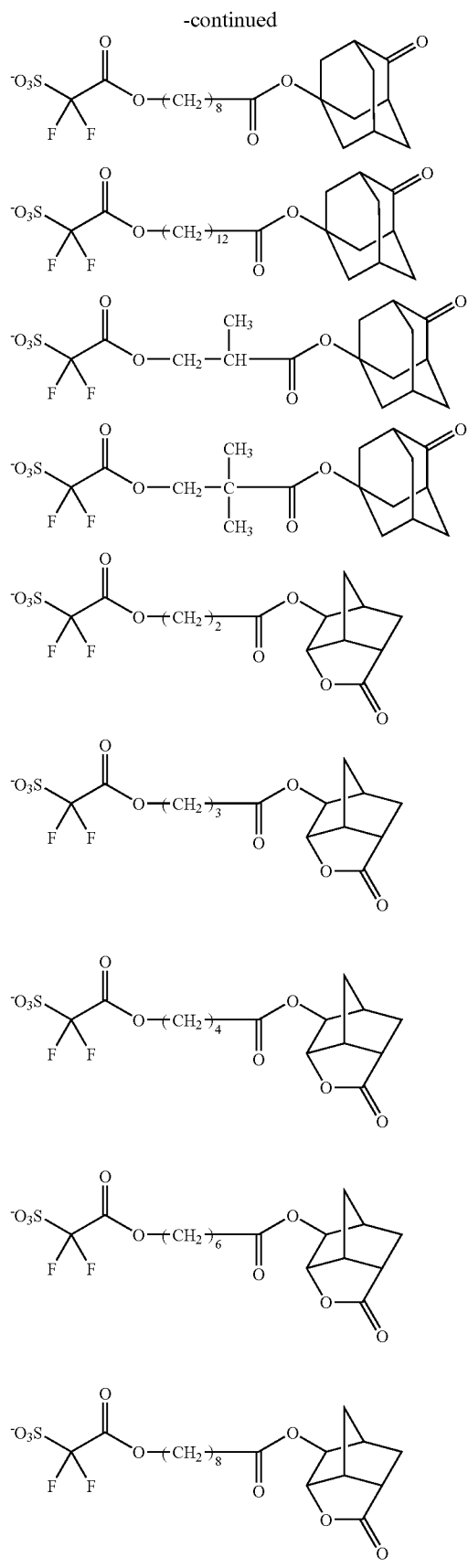
-continued
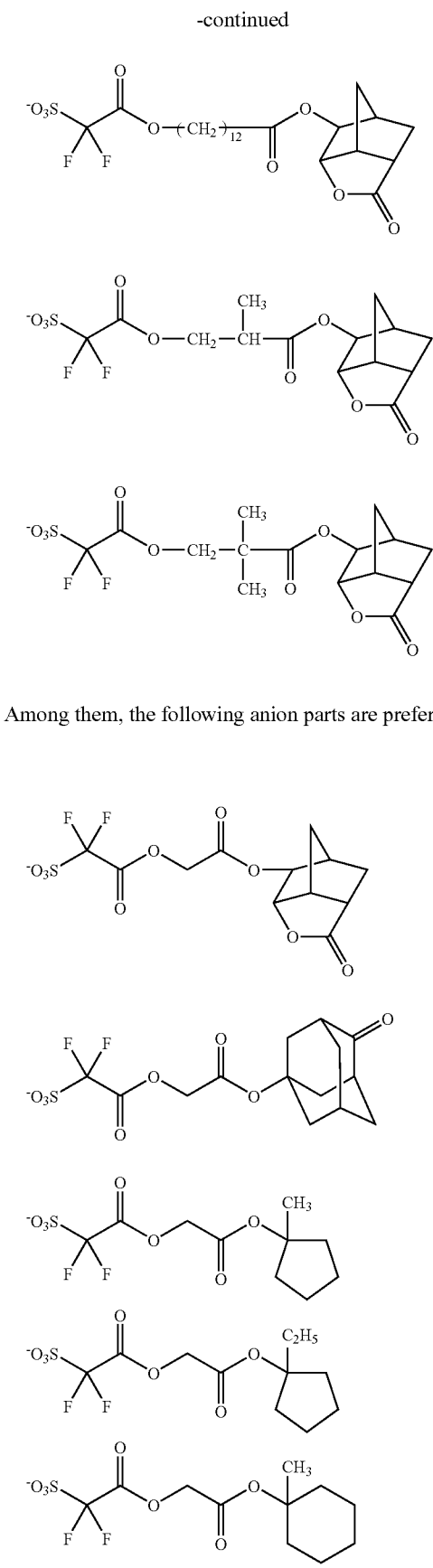
Among them, the following anion parts are preferable.

-continued

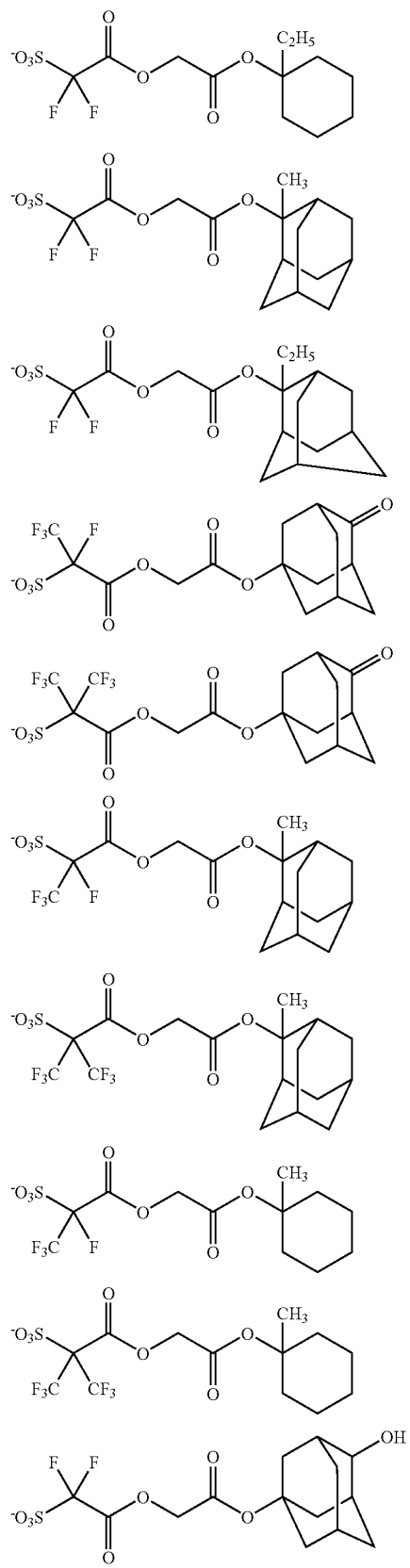

The following anon parts are more preferable.

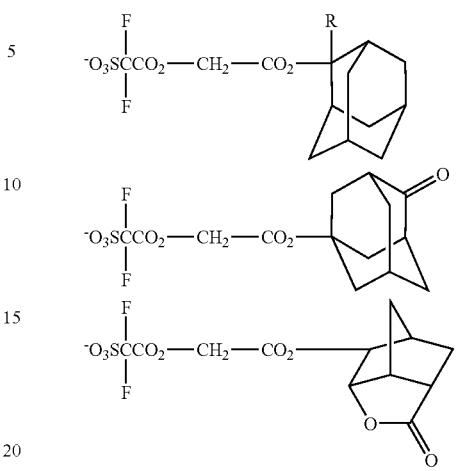

In the above formula, R represents the same meanings as above.

In the formula (I), $A^+$ represents an organic counter ion.
Examples of the organic counter ion include a cation represented by the formula (IIa):

(IIa)

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

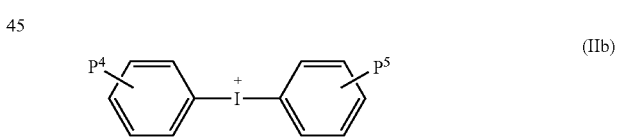

(IIb)

wherein $P^4$ and $P^5$ each independently represent a hydrogen atom, a hydroxyl group, a C1-C12 alkyl group or a C1-C12 alkoxy group, a cation represented by the formula (IIc):

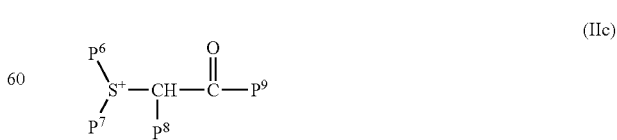

(IIc)

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent S⁺, and at least one —CH$_2$— in the divalent acyclic hydrocarbon group may be substituted with —CO—, —O— or —S—, P$^8$ represents a hydrogen atom, P$^9$ represents a C1-C12 alkyl group, a C3-C12 cycloalkyl group or an aromatic group which may be substituted, or P$^8$ and P$^9$ bond to form a divalent acyclic hydrocarbon group which forms a 2-oxocycloalkyl group together with the adjacent —CHCO—, and at least one —CH$_2$— in the divalent acyclic hydrocarbon group may be substituted with —CO—, —O— or —S—, and a cation represented by the formula (IId):

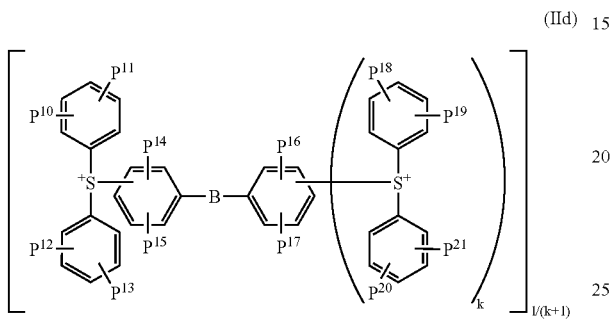

(IId)

wherein P$^{10}$, P$^{11}$, P$^{12}$, P$^{13}$, P$^{14}$, P$^{15}$, P$^{16}$, P$^{17}$, P$^{18}$, P$^{19}$, P$^{20}$ and P$^{21}$ each independently represent a hydrogen atom, a hydroxyl group, a C1-C12 alkyl group or a C1-C12 alkoxy group, B represents a sulfur or oxygen atom and k represents 0 or 1.

Examples of the C1-C12 alkoxy group in the formula (IIa) include a methoxy, ethoxy, n-propoxy, isopropoxy, n-butoxy, isobutoxy, sec-butoxy, tert-butoxy, n-pentyloxy, n-hexyloxy, n-octyloxy and 2-ethylhexyloxy group. Examples of the C3-C12 cyclic hydrocarbon group in the formula (IIa) include a cyclopentyl, cyclohexyl, 1-adamantyl, 2-adamantyl, phenyl, 2-methylphenyl, 4-methylphenyl, 1-naphthyl and 2-naphthyl group.

Examples of the C1-C30 alkyl group which may be substituted with at least one selected from the hydroxyl group, the C3-C12 cyclic hydrocarbon group and the C1-C12 alkoxy group in the formula (IIa) include a methyl, ethyl, n-propyl, isopropyl, n-butyl, isobutyl, sec-butyl, tert-butyl, n-pentyl, n-hexyl, n-octyl, 2-ethylhexyl and benzyl group.

Examples of the C3-C30 cyclic hydrocarbon group which may be substituted with at least one selected from the hydroxyl group and the C1-C12 alkoxy group in the formula (IIa) include a cyclopentyl, cyclohexyl, 1-adamantyl, 2-adamantyl, bicyclohexyl, phenyl, 2-methylphenyl, 4-methylphenyl, 4-ethylphenyl, 4-isopropylphenyl, 4-tert-butylphenyl, 2,4-dimethylphenyl, 2,4,6-trimethylphenyl, 4-n-hexylphenyl, 4-n-octylphenyl, 1-naphthyl, 2-naphthyl, fluorenyl, 4-phenylphenyl, 4-hydroxyphenyl, 4-methoxyphenyl, 4-tert-butoxyphenyl, 4-n-hexyloxyphenyl group.

Examples of the C1-C12 alkyl group in the formulae (IIb), (IIc) and (IId) include a methyl, ethyl, n-propyl, isopropyl, n-butyl, isobutyl, sec-butyl, tert-butyl, n-pentyl, n-hexyl, n-octyl and 2-ethylhexyl group. Examples of the C1-C12 alkoxy group in the formulae (IIb) and (IId) include the same groups as mentioned in the above formula (IIa).

Examples of the C3-C12 cycloalkyl group in the formula (IIc) include a cyclopropyl, cyclobutyl, cyclopentyl, cyclohexyl, cycloheptyl, cyclooctyl and cyclodecyl group. Examples of the C3-C12 divalent acyclic hydrocarbon group formed by bonding P$^6$ and P$^7$ include a trimethylene, tetramethylene and pentamethylene group. Examples of the ring group formed together with the adjacent S⁺ and the divalent acyclic hydrocarbon group include a tetramethylenesulfonio, pentamethylenesulfonio and oxybisethylenesulfonio group.

Examples of the aromatic group in the formula (IIc) include a phenyl, tolyl, xylyl and naphthyl group. Examples of the divalent acyclic hydrocarbon group formed by bonding P$^8$ and P$^9$ include a methylene, ethylene, trimethylene, tetramethylene and pentamethylene group and examples of the 2-oxocycloalkyl group formed together with the adjacent —CHCO— and the divalent acyclic hydrocarbon group include a 2-oxocyclopentyl and 2-oxocyclohexyl group.

The cation represented by the formula (IIa) or (IIc) is preferable and the cation represented by the formula (IIa) is more preferable.

In the cation represented by the formula (IIa), cations represented by the following formulae (IIIa), (IIIb) and (IIIc) are preferable, and the cation represented by the formula (IIIa) is more preferable.

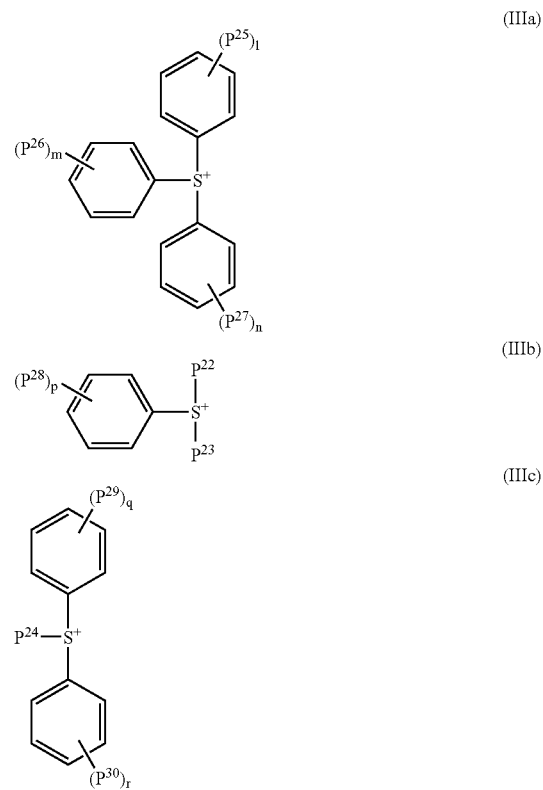

P$^{22}$, P$^{23}$ and P$^{24}$ each independently represent a C1-C20 alkyl group or a C3-C30 cyclic hydrocarbon group except a phenyl group. At least one hydrogen atom in the C1-C20 alkyl group in the formulae (IIIa), (IIIb) and (IIIc) may be substituted with a hydroxyl group, a C1-C12 alkoxy group or a C3-C12 cyclic hydrocarbon group. At least one hydrogen atom in the C3-C30 cyclic hydrocarbon group may be substituted with a hydroxyl group, a C1-C12 alkyl group or a C1-C12 alkoxy group. Examples of the alkyl group, the alkoxy group and the cyclic hydrocarbon group include the same groups as mentioned above.

$P^{25}$, $P^{26}$, $P^{27}$, $P^{28}$, $P^{29}$ and $P^{30}$ each independently represent a hydroxyl group, a C1-C12 alkyl group, a C1-C12 alkoxy group or a C3-C12 cyclic hydrocarbon group, and l, m, n, p, q and r each independently represent an integer of 0 to 5. Examples of the alkyl group, the alkoxy group and the cyclic hydrocarbon group include the same groups as mentioned above.

Examples of the cation represented by the formula (IIa) include the followings.

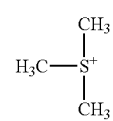 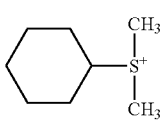

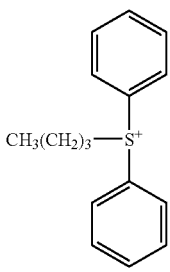 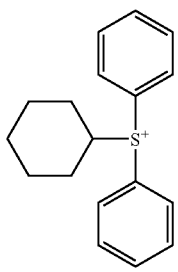

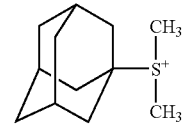 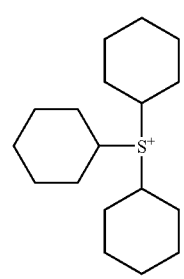

-continued

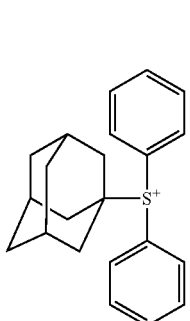 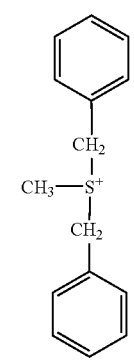 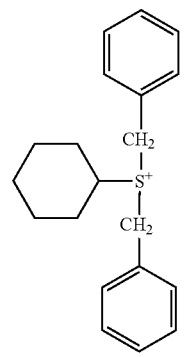

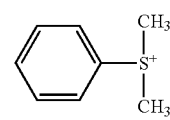 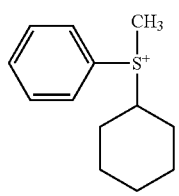

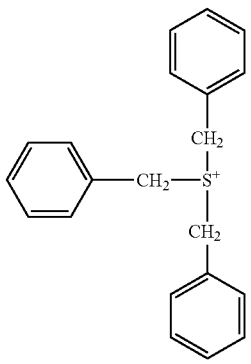 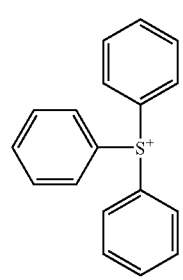

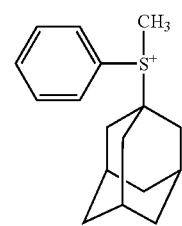 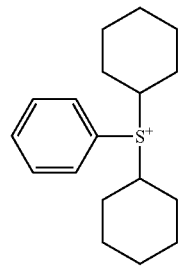

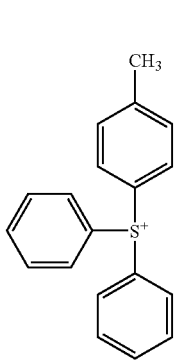 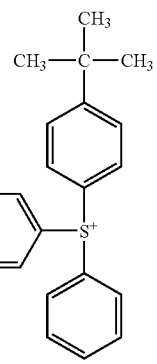

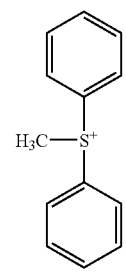 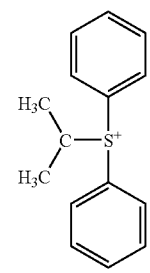

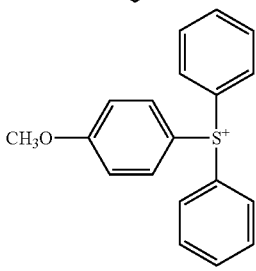 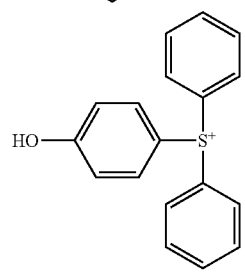

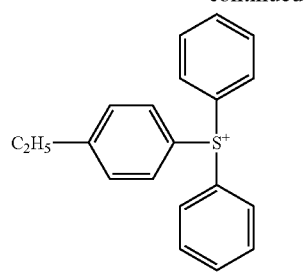
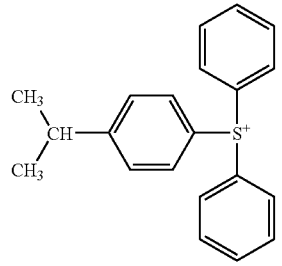
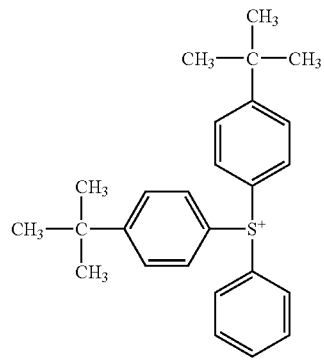
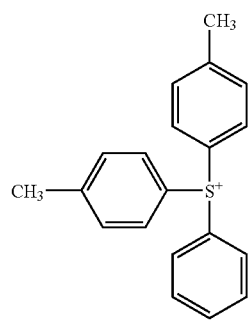
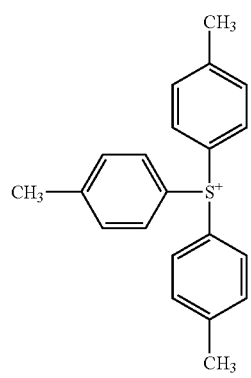
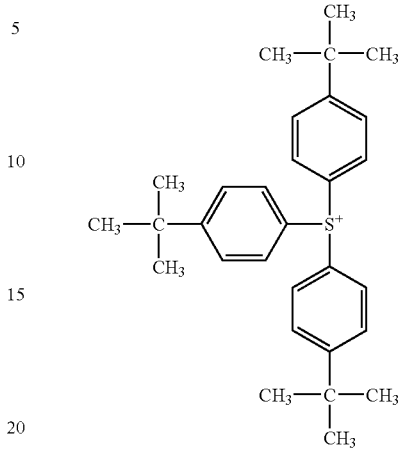
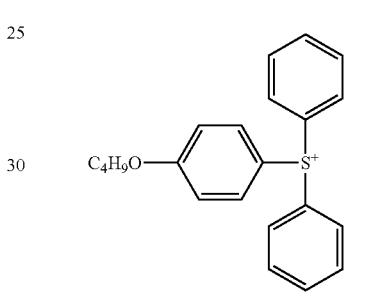
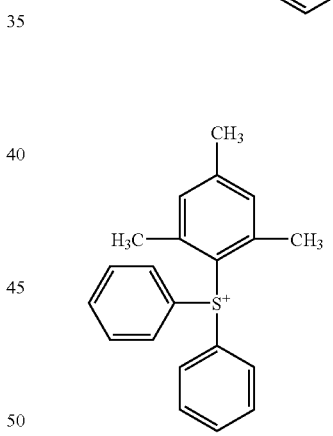
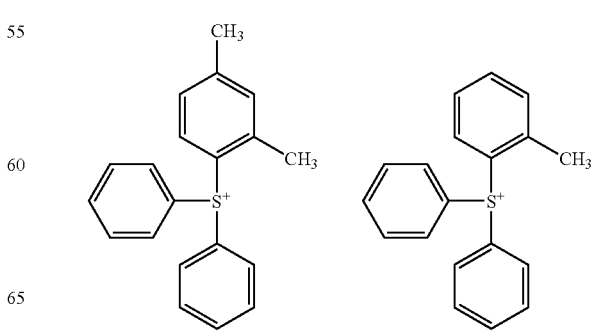

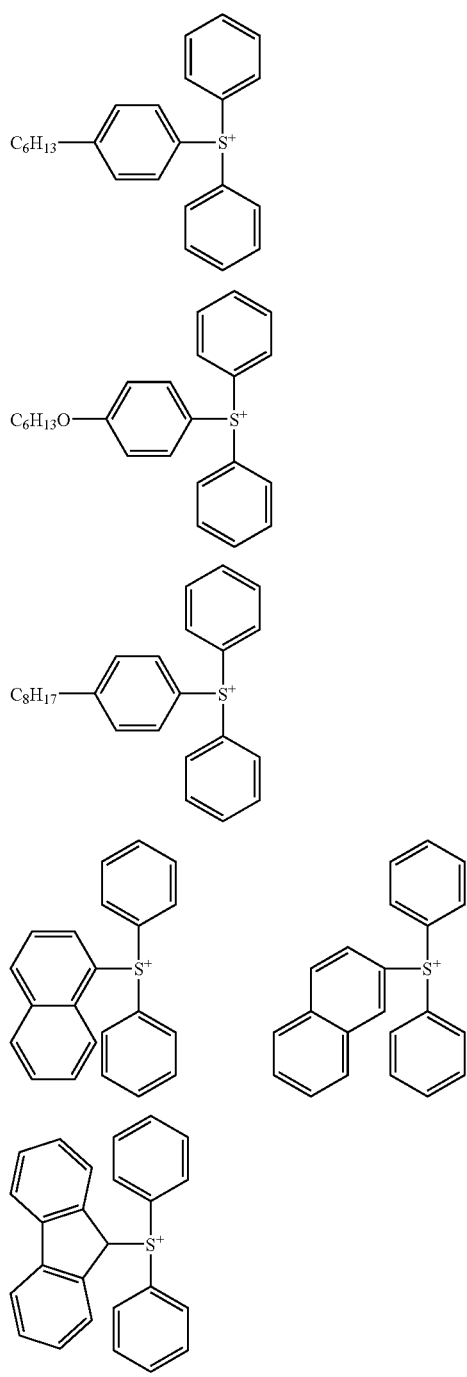
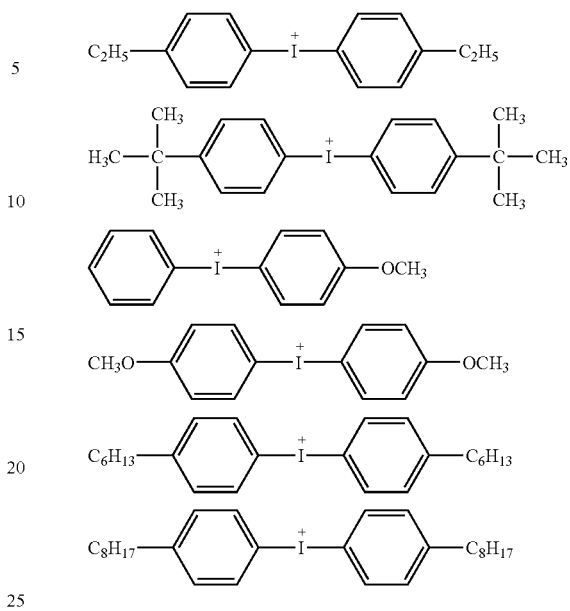
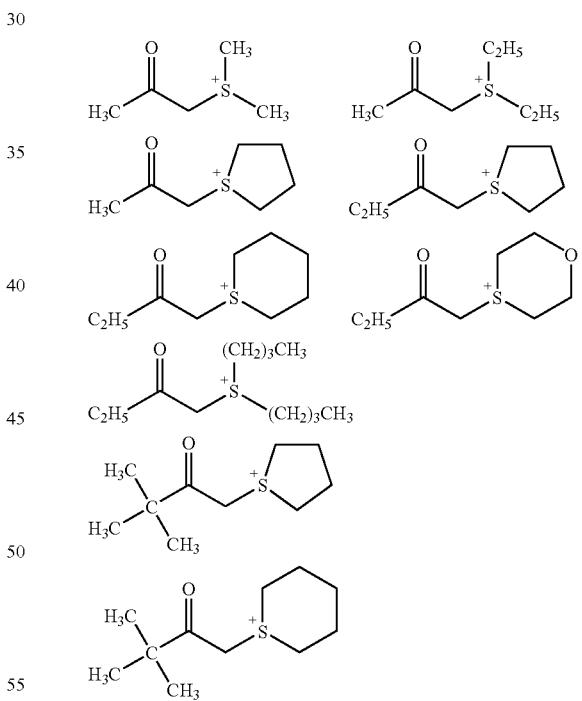
Examples of the cation represented by the formula (IIb) include the followings.
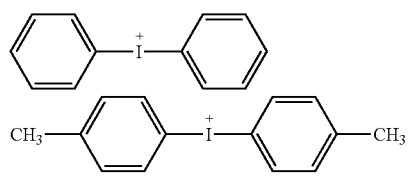
Examples of the cation represented by the formula (IIc) include the followings.
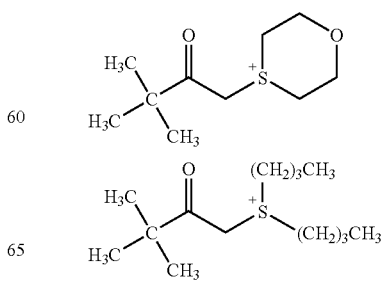

-continued
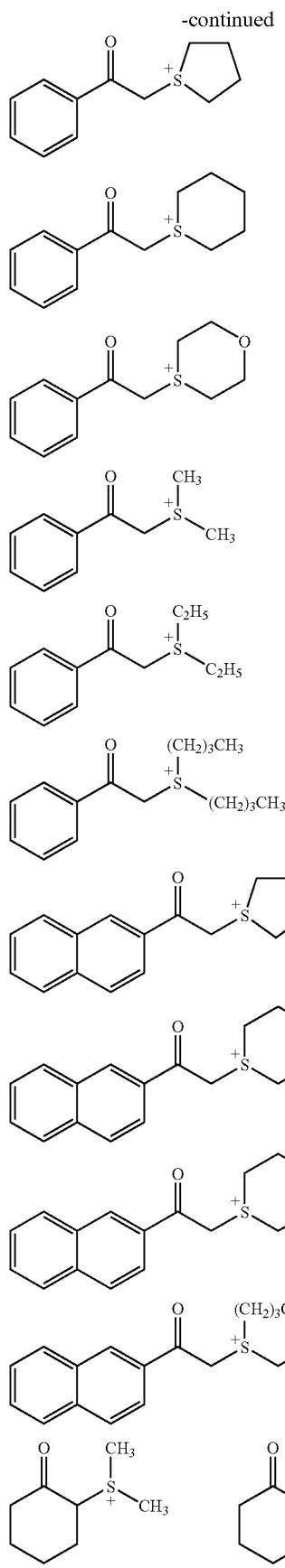
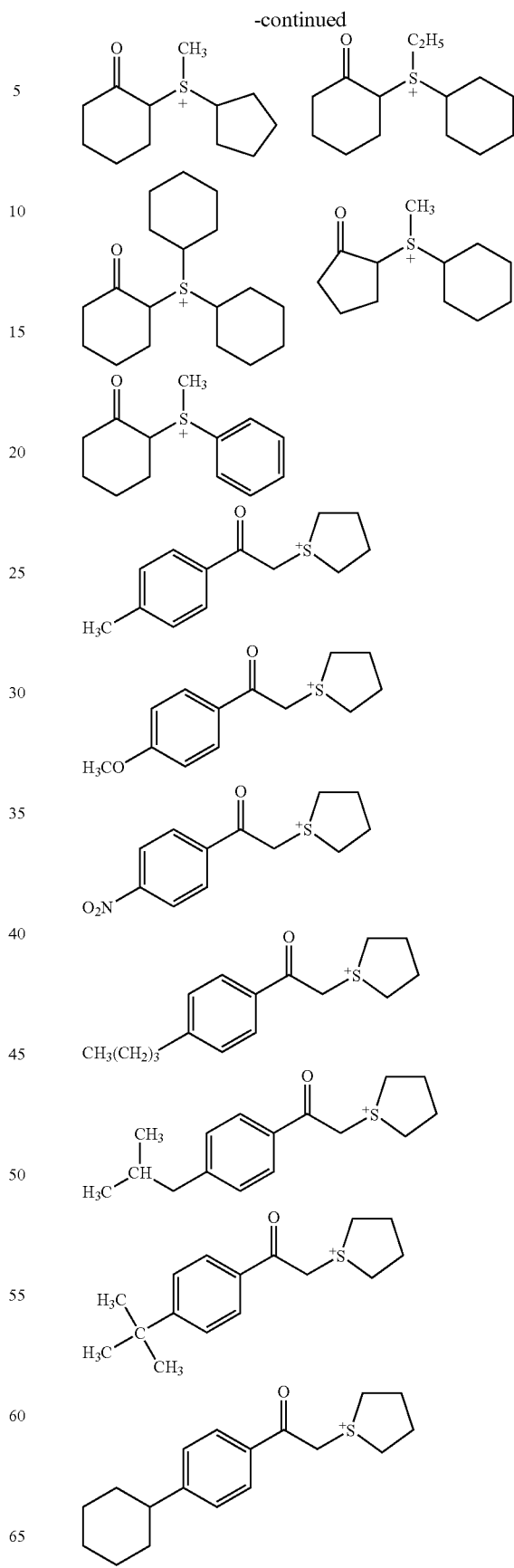

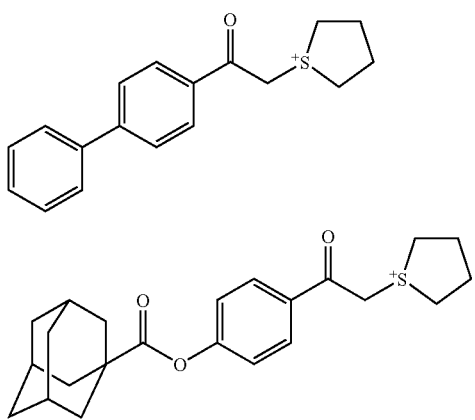
Examples of the cation represented by the formula (IId) include the followings.
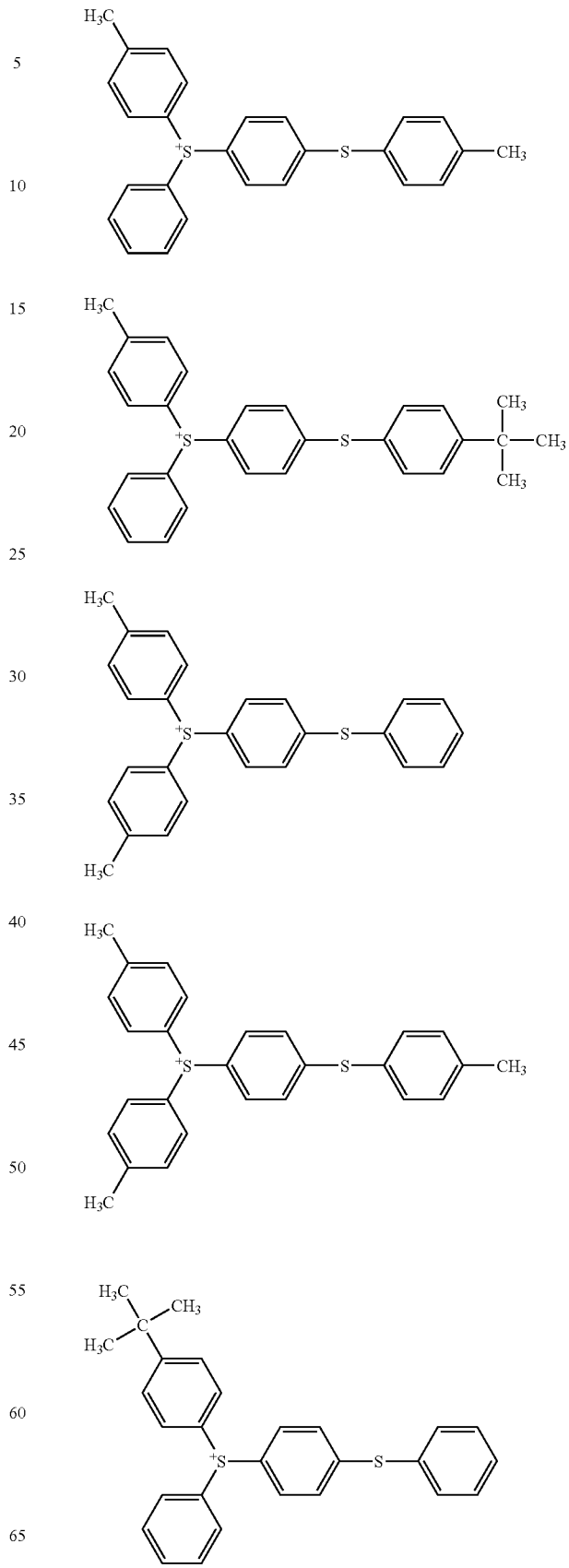

-continued
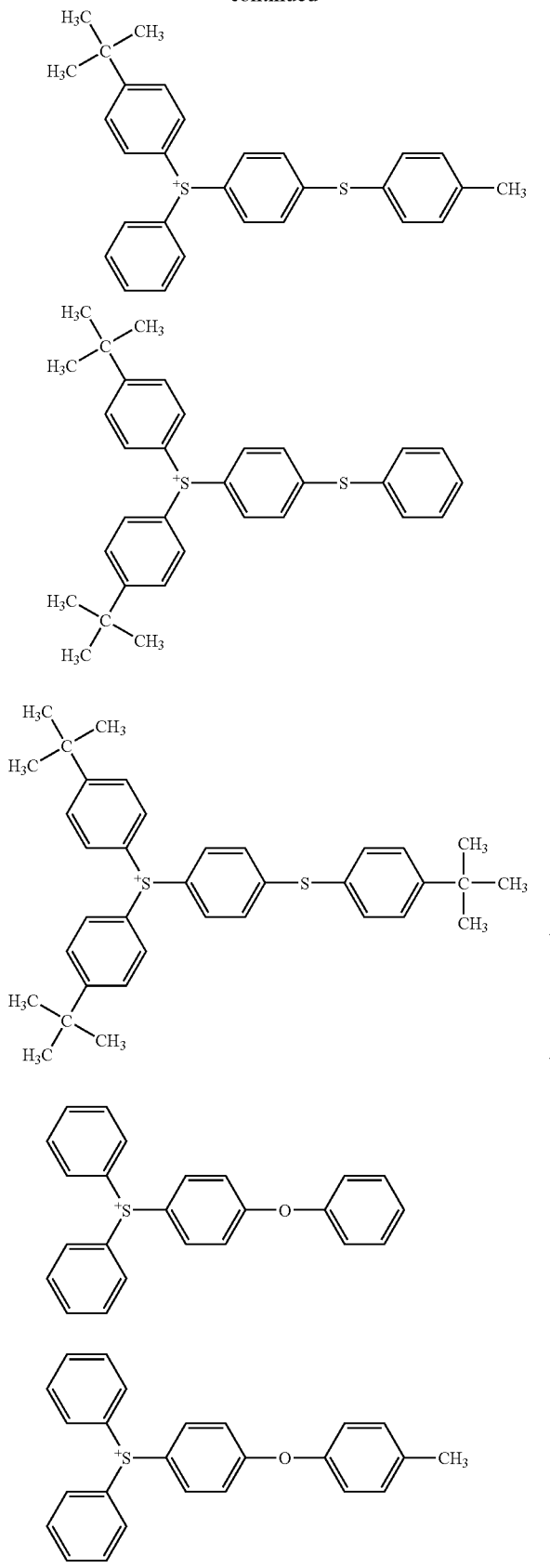
-continued
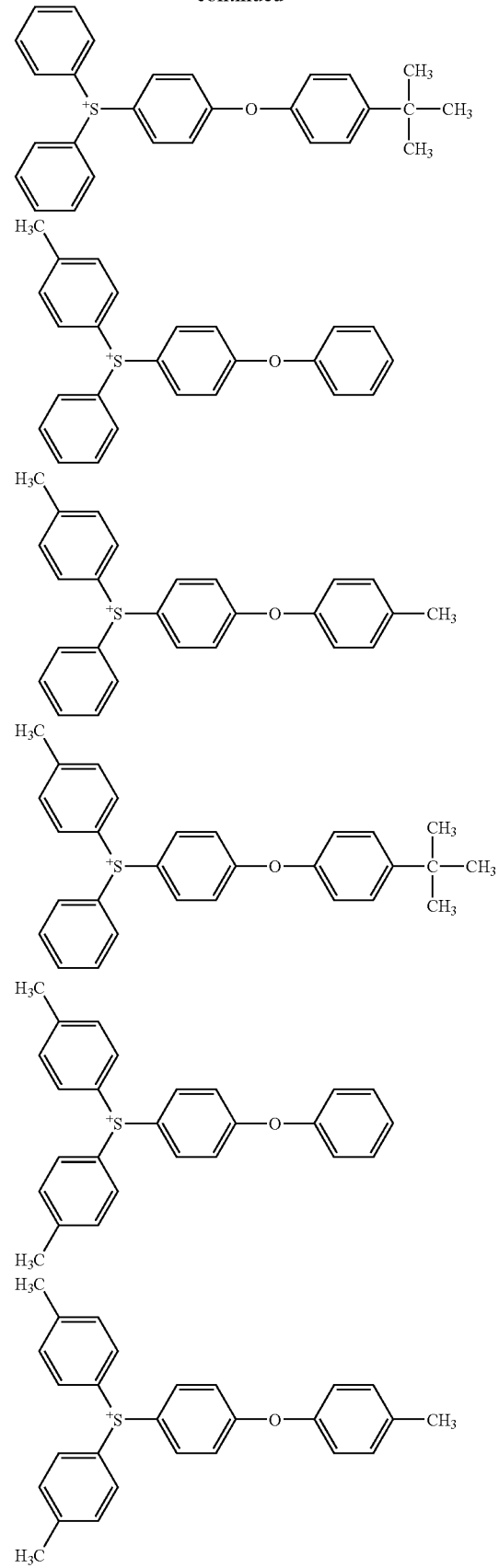

-continued
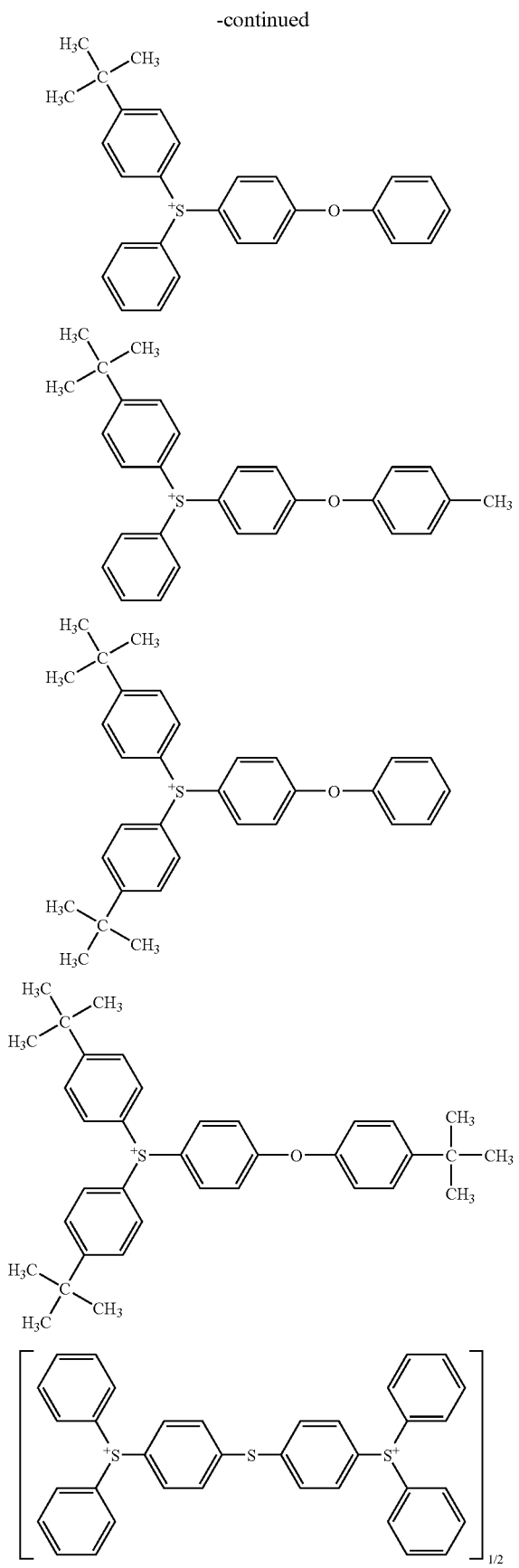
-continued
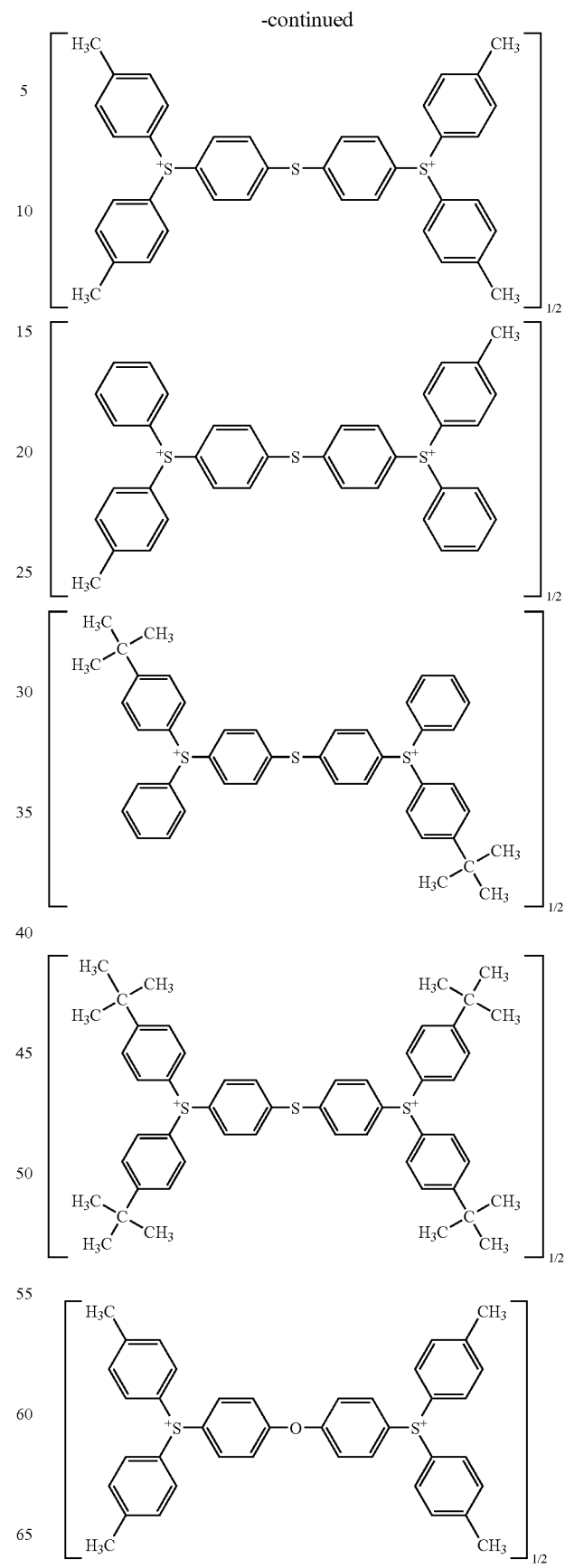

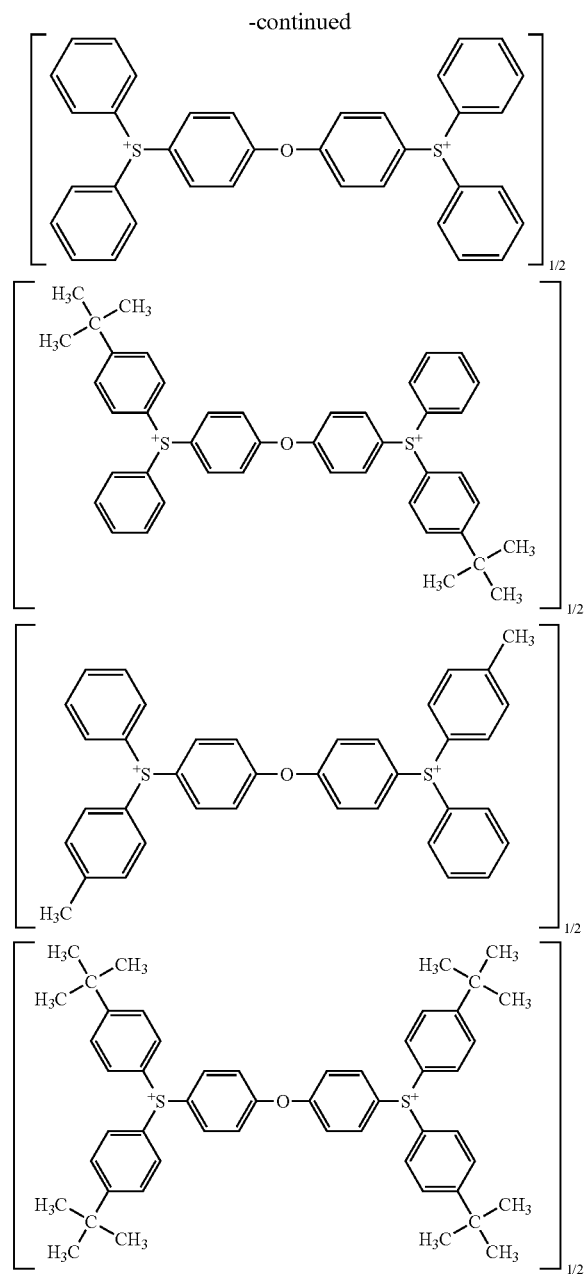

As Salt (I), the salts represented by the formulae (IVa), (IVb) and (IVc):

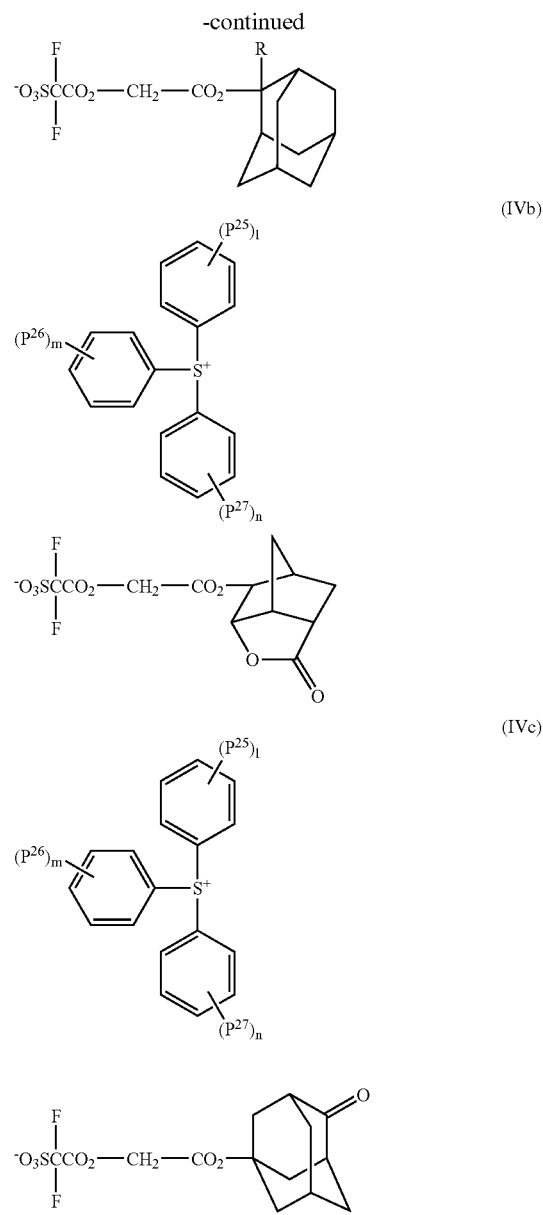

wherein $P^{25}$, $P^{26}$, $P^{27}$, l, m and n are the same as defined above, and R represents a C1-C6 alkyl group, are preferred for providing a chemically amplified resist composition giving patterns having good resolution and excellent exposure margin.

Examples of the process for production of Salt (I) include a process comprising reacting a salt represented by the formula (V):

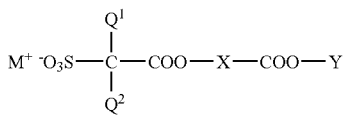

wherein X, Y, $Q^1$ and $Q^2$ are the same as defined above and M represents Li, Na, K or Ag (hereinafter, simply referred to as the salt (V)), with a compound represented by the formula (VIII):

$$A^+L^- \quad \text{(VIII)}$$

wherein $A^+$ is as defined above and L represents F, Cl, Br, I, $BF_4$, $AsF_6$, $SbF_6$, $PF_6$ or $ClO_4$ (hereinafter, simply referred to as the compound(VIII)), in an inert solvent such as acetonitrile, water, methanol, chloroform and dichloromethane, at a temperature of 0 to 150° C., preferably of 0 to 100° C.

As the compound (VIII), commercially available one is usually used.

The amount of the compound (VIII) to be used is usually 0.5 to 2 moles relative to 1 mole of the salt (V). Salt (I) obtained may be taken out by crystallization or washing with water.

Salt (I) can be also produced by a process which comprised reacting of a salt represented by the formula (IX):

wherein $Q^1$, $Q^2$ and $A^+$ are the same as defined above (hereinafter, simply referred to as the salt (IX)), with a compound represented by the formula (VI):

$$Z\text{-}X\text{—COO—}Y \quad \text{(VI)}$$

wherein X and Y are the same as defined above and Z represents Cl, Br or I (hereinafter, simply referred to as the compound (VI)), in a polar solvent such as acetone, acetonitrile and N,N-dimethylformamide, at a temperature of 0 to 150° C., preferably of 20 to 120° C.

The reaction of the salt (IX) and the compound (VI) is usually conducted in the presence of a base, and examples of the base include an inorganic base such as potassium carbonate. The reaction may be conducted, if necessary, in the presence of potassium iodide and the like.

The amount of the salt (IX) is usually 0.2 to 3 moles, preferably 0.5 to 2 moles relative to 1 mole of the compound (VI).

The salt (V) can be produced by a process which comprises reacting the compound (VI) with a compound represented by the formula (VII):

wherein $Q^1$, $Q^2$ and M are the same as defined above (hereinafter, simply referred to as the compound (VII)).

The reaction of the compound (VI) and the compound (VII) is usually conducted by mixing both in a polar solvent such as acetone, acetonitrile and N,N-dimethylformamide, at 0 to 150° C., preferably 20 to 120° C. in the presence of a base catalyst such as potassium carbonate.

The reaction may be conducted, if necessary, in the presence of potassium iodide and the like.

The amount of the compound (VII) to be used is usually 0.2 to 3 moles, preferably 0.2 to 3 moles relative to 1 mole of the compound (VI).

The salt (IX) can be produced by a process which comprises reacting the compound (VII) with the compound (VIII).

The process is usually conducted in an inert solvent such as water, acetonitrile, chloroform and dichloromethane, at a temperature of 0 to 100° C., preferably of 0 to 60° C.

The amount of the compound (VIII) is usually 0.5 to 2 moles relative to 1 mole of the compound (VII).

Next, the present chemically amplified positive resist composition will be illustrated.

The present chemically amplified positive resist composition comprises Salt (I) and a resin containing a structural unit which has an acid-labile group and which itself is insoluble or poorly soluble in an aqueous alkali solution but becomes soluble in an aqueous alkali solution by the action of an acid.

Salt (I) is usually used as an acid generator, and the acid generated by irradiation to Salt (I) catalytically acts against acid-labile groups in the resin, cleaves acid-labile groups, and the resin becomes soluble in an alkali aqueous solution. Such a composition is suitable for chemically amplified positive resist composition.

The resin used for the present composition contains a structural unit which has the acid-labile group and which itself is insoluble or poorly soluble in an alkali aqueous solution, but the acid-labile group cleave by an acid.

In the present specification, "—COOR" may be described as "a structure having ester of carboxylic acid", and may also be abbreviated as "ester group". Specifically, "—COOC$(CH_3)_3$" may be described as "a structure having tert-butyl ester of carboxylic acid", or be abbreviated as "tert-butyl ester group".

Examples of the acid-labile group include a structure having ester of carboxylic acid such as alkyl ester group in which a carbon atom adjacent to the oxygen atom is quaternary carbon atom, alicyclic ester group in which a carbon atom adjacent to the oxygen atom is quaternary carbon atom, and a lactone ester group in which a carbon atom adjacent to the oxygen atom is quaternary carbon atom. The "quaternary carbon atom" means a "carbon atom joined to four substituents other than hydrogen atom".

Examples of the acid-labile group include an alkyl ester group in which a carbon atom adjacent to the oxygen atom is quaternary carbon atom such as a tert-butyl ester group; an acetal type ester group such as a methoxymethyl ester, ethoxymethyl ester, 1-ethoxyethyl ester, 1-isobutoxyethylester, 1-isopropoxyethylester, 1-ethoxypropoxyester, 1-(2-methoxyethoxy)ethyl ester, 1-(2-acetoxyethoxy)ethyl ester, 1-[2-(1-adamantyloxy)ethoxy]ethyl ester, 1-[2-(1-adamantanecarbonyloxy)ethoxy]ethyl ester, tetrahydro-2-furyl ester and tetrahydro-2-pyranyl ester group; an alicyclic ester group in which a carbon atom adjacent to the oxygen atom is quaternary carbon atom, such as an isobornyl ester, 1-alkylcycloalkyl ester, 2-alkyl-2-adamantyl ester and 1-(1-adamantyl)-1-alkylalkyl ester group.

At least one hydrogen atom in the adamantyl group may be substituted with a hydroxyl group.

Examples of the structural unit include a structure unit derived from an ester of acrylic acid, a structural unit derived from an ester of methacrylic acid, a structural unit derived from an ester of norbornenecarboxylic acid, a structural unit derived from an ester of tricyclodecenecarboxylic acid and a structural unit derived from an ester of tetracyclodecenecarboxylic acid. The structure units derived from the ester of acrylic acid and from the ester of methacrylic acid are preferable.

The resin used for the present composition can be obtained by conducting polymerization reaction of a monomer or monomers having the acid-labile group and an olefinic double bond.

Among the monomers, those having a bulky and acid-labile group such as an alicyclic ester group (e.g. a 2-alkyl-2-adamantyl ester and 1-(1-adamantyl)-1-alkylalkyl ester group), since excellent resolution is obtained when the resin obtained is used in the present composition.

Examples of such monomer containing the bulky and acid-labile group include a 2-alkyl-2-adamantyl acrylate, a 2-alkyl-2-adamantyl methacrylate, 1-(1-adamantyl)-1-alkylalkyl acrylate, a 1-(1-adamantyl)-1-alkylalkyl methacrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate and a 1-(1-adamantyl)-1-alkylalkyl α-chloroacrylate.

Particularly when the 2-alkyl-2-adamantyl acrylate, the 2-alkyl-2-adamantyl methacrylate or the 2-alkyl-2-adamantyl α-chloroacrylate is used as the monomer for the resin component in the present composition, a resist composition having excellent resolution tend to be obtained. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantyl acrylate, 2-methyl-2-adamantyl α-chloroacrylate and 2-ethyl-2-adamantyl α-chloroacrylate. When particularly 2-ethyl-2-adamantyl acrylate, 2-ethyl-2-adamantyl methacrylate, 2-isopropyl-2-adamantyl acrylate or 2-isopropyl-2-adamantyl methacrylate is used for the present composition, a resist composition having excellent sensitivity and heat resistance tends to be obtained.

In the present invention, two or more kinds of monomers having a group or groups dissociated by the action of the acid may be used together, if necessary.

The 2-alkyl-2-adamantyl acrylate can be usually produced by reacting a 2-alkyl-2-adamantanol or a metal salt thereof with an acrylic halide, and the 2-alkyl-2-adamantyl methacrylate can be usually produced by reacting a 2-alkyl-2-adamantanol or a metal salt thereof with a methacrylic halide.

The resin used for the present composition can also contain other structural unit or units derived from an acid-stable monomer in addition to the above-mentioned structural units having the acid-labile group.

Herein, the "structural unit derived from an acid-stable monomer" means "a structural unit not dissociated by an acid generated from Salt (I)".

Examples of such other structural unit derived from the acid-stable monomer include a structural unit derived from a monomer having a free carboxyl group such as acrylic acid and methacrylic acid; a structural unit derived from an aliphatic unsaturated dicarboxylic anhydride such as maleic anhydride and itaconic anhydride; a structural unit derived from 2-norbornene; a structural unit derived from acrylonitrile or methacrylonitrile; a structural unit derived from an alkyl acrylate or an alkyl methacrylate in which a carbon atom adjacent to oxygen atom is secondary or tertiary carbon atom; a structural unit derived from 1-adamantyl acrylate or 1-adamantyl methacrylate; a structural unit derived from styrene monomer such as p-hydroxystyrene and m-hydroxystyrene; a structural unit derived from acryloyloxy-γ-butyrolactone or methacryloyloxy-γ-butyrolactone having a lactone ring which may be substituted with an alkyl group; and the like. Herein, the 1-adamantyloxycarbonyl group is the acid-stable group though the carbon atom adjacent to oxygen atom is the quaternary carbon atom, and the 1-adamantyloxycarbonyl group may be substituted with at least one hydroxyl group.

Specific examples of the structural unit derived from the acid-stable monomer include a structural unit derived from 3-hydroxy-1-adamantyl acrylate;

a structural unit derived from 3-hydroxy-1-adamantyl methacrylate;

a structural unit derived from 3,5-dihydroxy-1-adamantyl acrylate;

a structural unit derived from 3,5-dihydroxy-1-adamantyl methacrylate;

a structural unit derived from α-acryloyloxy-γ-butyrolactone;

a structural unit derived from α-methacryloyloxy-γ-butyrolactone;

a structural unit derived from β-acryloyloxy-γ-butyrolactone;

a structural unit derived from β-methacryloyloxy-γ-butyrolactone;

a structural unit represented by the formula (X):

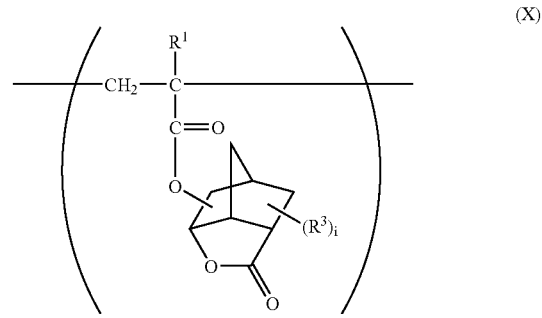

wherein $R^1$ represents a hydrogen atom or a methyl group, $R^3$ represents a methyl group, a trifluoromethyl group or a halogen atom, i represents an integer of 0 to 3, and when i represents 2 or 3, $R^3$s may be the same or different each other;

a structural unit represented by the formula (XI):

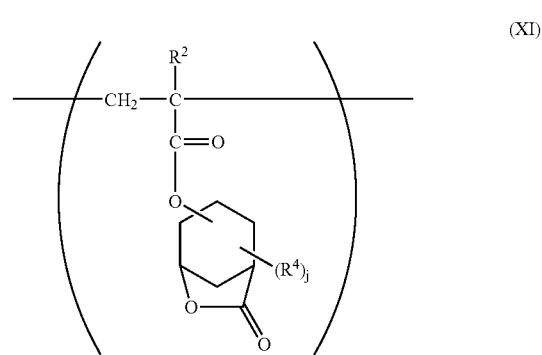

wherein $R^2$ represents a hydrogen atom or a methyl group, $R^4$ represents a methyl group, a trifluoromethyl group or a halogen atom, j represents an integer of 0 to 3, and when j represents 2 or 3, $R^4$s may be the same or different each other;

a structural unit derived from p-hydroxystyrene;

a structural unit derived from m-hydroxystyrene;

a structural unit derived from an alicyclic compound having an olefinic double bond such as a structural unit represented by the formula (XII):

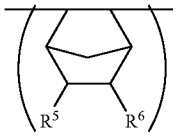
(XII)

wherein $R^5$ and $R^6$ each independently represents a hydrogen atom, a C1-C3 alkyl group, a C1-C3 hydroxyalkyl group, a carboxyl group, a cyano group, a hydroxyl group or a —COOU group in which U represents an alcohol residue, or $R^5$ and $R^6$ can be bonded together to form a carboxylic anhydride residue represented by —C(=O)OC(=O)—;

a structural unit derived from an aliphatic unsaturated dicarboxylic anhydride such as a structural unit represented by the formula (XIII):

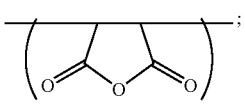
(XIII)

a structural unit represented by the formula (XIV):

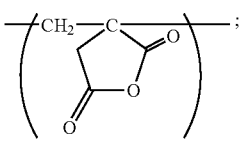
(XIV)

and the like.

Particularly, the resin having further at least one structural unit selected from the structural unit derived from p-hydroxystyrene, the structural unit derived from m-hydroxystyrene, the structural unit derived from 3-hydroxy-1-adamantyl acrylate, the structural unit derived from 3-hydroxy-1-adamantyl methacrylate, the structural unit derived from 3,5-dihydroxy-1-adamantyl acrylate, the structural unit derived from 3,5-dihydroxy-1-adamantyl methacrylate, the structural unit represented by the formula (X) and the structural unit represented by the formula (XI) in addition to the structural unit having the acid-labile group is preferable from the standpoint of the adhesiveness of resist to a substrate and resolution of resist.

3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting corresponding hydroxyadamantane with acrylic acid, methacrylic acid or its acid halide, and they are also commercially available.

Further, the acryloyloxy-γ-butyrolactone and the methacryloyloxy-γ-butyrolactone having the lactone ring which may be substituted with the alkyl group can be produced by reacting corresponding α- or β-bromo-γ-butyrolactone with acrylic acid or methacrylic acid, or reacting corresponding α- or β-hydroxy-γ-butyrolactone with the acrylic halide or the methacrylic halide.

As monomers to give structural units represented by the formulae (X) and (XI), specifically listed are, for example, an acrylate of alicyclic lactones and a methacrylate of alicyclic lactones having the hydroxyl group described below, and mixtures thereof. These esters can be produced, for example, by reacting the corresponding alicyclic lactone having the hydroxyl group with acrylic acid or methacrylic acid, and the production method thereof is described in, for example, JP 2000-26446 A.

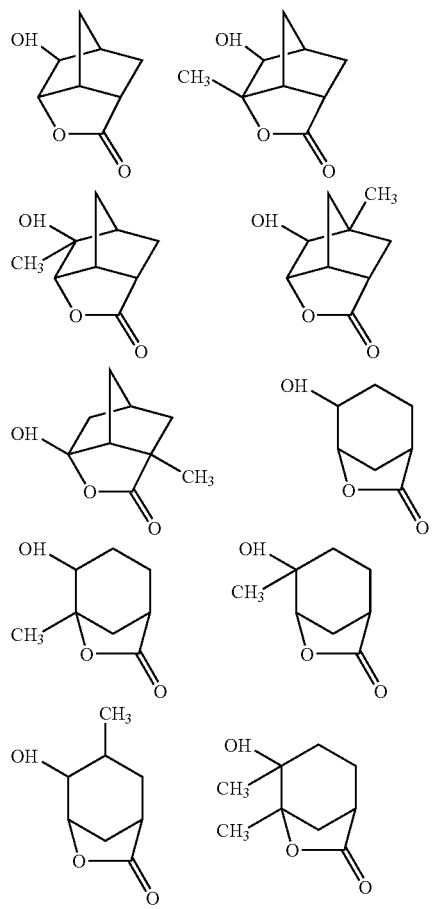

Examples of the acryloyloxy-γ-butyrolactone and the methacryloyloxy-γ-butyrolactone having the lactone ring which may be substituted with the alkyl group include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone and β-methacryloyloxy-α-methyl-γ-butyrolactone.

In the case of KrF lithography, even in the case of using a structure unit derived from hydroxystyrene such as p-hydroxystyrene and m-hydroxystyrene, as one of components of the resin, a resist composition having sufficient transparency can be obtained. For obtaining such copolymerization resins, the corresponding acrylic or methacrylic ester monomer can be radical-polymerized with acetoxystyrene and styrene, and then the acetoxy group in the structure unit derived from acetoxystyrene can be de-acetylated with an acid.

The resin containing a structural unit derived from 2-norbornene shows strong structure because the alicyclic group is directly present on its main chain and shows a property that dry etching resistance is excellent. The structural unit derived from 2-norbornene can be introduced into the main chain by radical polymerization using, for example, an aliphatic unsaturated dicarboxylic anhydride such as maleic anhydride and itaconic anhydride together in addition to corresponding 2-norbornene. The structural unit derived from 2-norbornene is formed by opening of its double bond, and can be represented by the above-mentioned formula (XII). The structural unit derived from maleic anhydride and from itaconic anhydride which are the structural unit derived from aliphatic unsaturated dicarboxylic anhydrides are formed by opening of their double bonds, and can be represented by the above-mentioned formula (XIII) and the formula (XIV), respectively.

In $R^5$ and $R^6$, examples of the C1-C3 alkyl group include a methyl, ethyl and n-propyl group, and examples of the C1-C3 hydroxyalkyl group include a hydroxymethyl and 2-hydroxyethyl group.

In $R^5$ and $R^6$, the —COOU group is an ester formed from the carboxyl group, and as the alcohol residue corresponding to U, for example, an optionally substituted C1-C8 alkyl group, 2-oxooxolan-3-yl group, 2-oxooxolan-4-yl and the like are listed, and as the substituent on the C1-C8 alkyl group, a hydroxyl group, an alicyclic hydrocarbon residue and the like are listed.

Specific examples of the monomer used to give the structural unit represented by the above-mentioned formula (XII) may include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When U in the —COOU group is the acid-labile group, the structural unit represented by the formula (XII) is a structural unit having the acid-labile group even if it has the norbornane structure. Examples of monomers giving structural unit having the acid-labile group include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate, 1-(1-adamantyl)-1-methylethyl 5-norbornene-2-carboxylate, and the like.

The resin used in the present composition preferably contains the structural unit or units having the acid-labile group generally in a ratio of 10 to 80% by mole in all structural units of the resin though the ratio varies depending on the kind of radiation for patterning exposure, the kind of the acid-labile group, and the like.

When the structural units particularly derived from the 2-alkyl-2-adamantyl acrylate, the 2-alkyl-2-adamantyl methacrylate, the 1-(1-adamantyl)-1-alkylalkyl acrylate or the 1-(1-adamantyl)-1-alkylalkyl methacrylate are used as the structural unit having the acid-labile group, it is advantageous in dry-etching resistance of the resist that the ratio of the structural units is 15% by mole or more in all structural units of the resin.

When, in addition to structural units having the acid-labile group, other structural units having the acid-stable group are contained in the resin, it is preferable that the sum of these structural units is in the range of 20 to 90% by mole based on all structural units of the resin.

The resin used for the present composition can be produced by conducting polymerization reaction of the corresponding monomer or monomers. The resin can be also produced by conducting oligomerization of the corresponding monomer or monomers followed by polymerizing the oligomer obtained.

The polymerization reaction is usually carried out in the presence of a radical initiator.

The radical initiator is not limited and examples thereof include an azo compound such as 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile), 2,2'-azobis(2,4-dimethyl-4-methoxyvaleronitrile), dimethyl-2,2'-azobis(2-methylpropionate) and 2,2'-azobis(2-hydroxymethylpropionitrile); an organic hydroperoxide such as lauroyl peroxide, tert-butyl hydroperoxide, benzoyl peroxide, tert-butyl peroxybenzoate, cumene hydroperoxide, diisopropyl peroxydicarbonate, di-n-propyl peroxydicarbonate, tert-butyl peroxyneodecanoate, tert-butyl peroxypivalate and 3,5,5-trimethylhexanoyl peroxide; and an inorganic peroxide such as potassium peroxodisulfate, ammonium peroxodisulfate and hydrogen peroxide. Among them, the azo compound is preferable and 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile) and dimethyl-2,2'-azobis(2-methylpropionate) are more preferable, and 2,2'-azobisisobutyronitrile and 2,2'-azobis(2,4-dimethylvaleronitrile) are especially preferable.

These radical initiators may be used alone or in a form of a mixture of two or more kinds thereof. When the mixture of two or more kinds thereof is used, the mixed ratio is not particularly limited.

The amount of the radical initiator is preferably 1 to 20% by mole based on all monomer or oligomer molar amount.

The polymerization temperature is usually 0 to 150° C., and preferably 40 to 100° C.

The polymerization reaction is usually carried out in the presence of a solvent and it is preferred to use a solvent which is sufficient to dissolve the monomer, the radical initiator and the resin obtained.

Examples thereof include a hydrocarbon solvent such as toluene; an ether solvent such as 1,4-dioxane and tetrahydrofuran; a ketone solvent such as methyl isobutyl ketone; an alcohol solvent such as isopropyl alcohol; a cyclic ester solvent such as γ-butyrolactone; a glycol ether ester solvent such as propylene glycol monomethyl ether acetate; and an acyclic ester solvent such as ethyl lactate. These solvents may be used alone and a mixture thereof may be used.

The amount of the solvent is not limited, and practically, it is preferably 1 to 5 parts by weight relative to 1 part of all monomers or oligomers.

When an alicyclic compound having an olefinic double bond and an aliphatic unsaturated dicarboxylic anhydride are used as monomers, it is preferable to use them in excess amount in view of a tendency that these are not easily polymerized.

After competition of the polymerization reaction, the resin produced can be isolated, for example, by adding a solvent in which the present resin is insoluble or poorly soluble to the reaction mixture obtained and filtering the precipitated resin.

If necessary, the isolated resin may be purified, for example, by washing with a suitable solvent.

The present resist composition preferably includes 80 to 99.9% by weight of the resin component and 0.1 to 20% by weight of Salt (I) based on the total amount of the resin component and Salt (I).

In the present resist composition, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

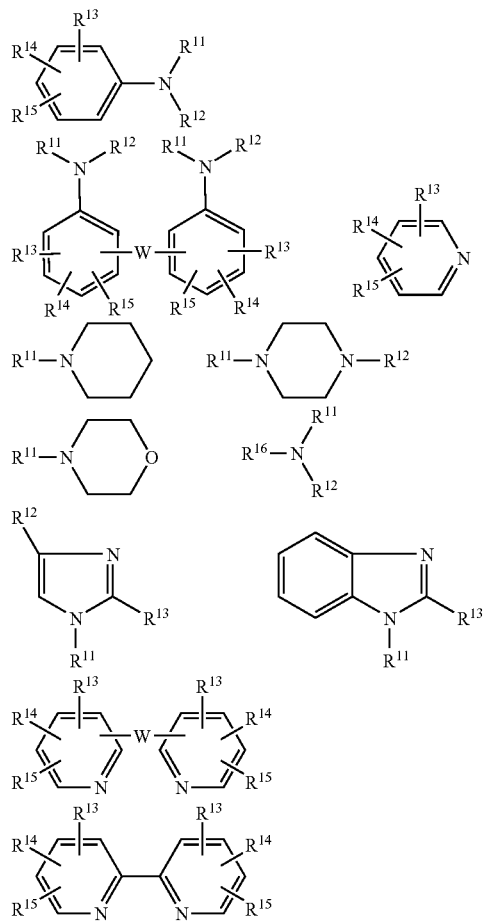

wherein $R^{11}$ and $R^{12}$ independently represent a hydrogen atom, an alkyl group, a cycloalkyl group or an aryl group, and the alkyl, cycloalkyl and aryl group may be substituted with at least one group selected from a hydroxyl group, an amino group which may be substituted with a C1-C4 alkyl group and a C1-C6 alkoxy group which may be substituted with a C1-C6 alkoxy group, $R^{13}$ and $R^{14}$ independently represent a hydrogen atom, an alkyl group, a cycloalkyl group, an aryl group or an alkoxy group, and the alkyl, cycloalkyl, aryl and alkoxy group may be substituted with at least one group selected from a hydroxyl group, an amino group which may be substituted with a C1-C4 alkyl group and a C1-C6 alkoxy group, or $R^{13}$ and $R^{14}$ bond together with the carbon atoms to which they bond to form an aromatic ring, $R^{15}$ represent a hydrogen atom, an alkyl group, a cycloalkyl group, an aryl group, an alkoxy group or a nitro group, and the alkyl, cycloalkyl, aryl and alkoxy group which may be substituted with at least one group selected from a hydroxyl group, an amino group which may be substituted with a C1-C4 alkyl group and a C1-C6 alkoxy group, $R^{16}$ represents an alkyl or cycloalkyl group, and the alkyl and cycloalkyl group may be substituted with at least one group selected from a hydroxyl group, an amino group which may be substituted with a C1-C4 alkyl group and a C1-C6 alkoxy group, and W represents —CO—, —NH—, —S—, —S—S—, an alkylene group of which at least one methylene group may be replaced with —O—, or an alkenylene group of which at least one methylene group may be replaced with —O—, and a quaternary ammonium hydroxide represented by the following formula:

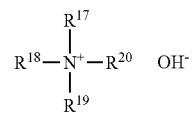

wherein $R^{17}$, $R^{18}$, $R^{19}$ and $R^{20}$ independently represent an alkyl group, a cycloalkyl group or an aryl group, and the alkyl, cycloalkyl and aryl group may be substituted with at least one group selected from a hydroxyl group, an amino group which may be substituted with a C1-C4 alkyl group and a C1-C6 alkoxy group.

The alkyl group in $R^{11}$, $R^{12}$, $R^{13}$, $R^{14}$, $R^{15}$, $R^{16}$, $R^{17}$, $R^{18}$, $R^{19}$ and $R^{20}$ preferably has about 1 to 10 carbon atoms, and more preferably has about 1 to 6 carbon atoms.

Examples of the amino group which may be substituted with the C1-C4 alkyl group include an amino, methylamino, ethylamino, n-butylamino, dimethylamino and diethylamino group. Examples of the C1-C6 alkoxy group which may be substituted with the C1-C6 alkoxy group include a methoxy, ethoxy, n-propoxy, isopropoxy, n-butoxy, tert-butoxy, n-pentyloxy, n-hexyloxy and 2-methoxyethoxy group.

Specific examples of the alkyl group which may be substituted with at least one group selected from a hydroxyl group, an amino group which may be substituted with a C1-C4 alkyl group, and a C1-C6 alkoxy group which may be substituted with a C1-C6 alkoxy group include a methyl, ethyl, n-propyl, isopropyl, n-butyl, tert-butyl, n-pentyl, n-hexyl, n-octyl, n-nonyl, n-decyl, 2-(2-methoxyethoxy)ethyl, 2-hydroxyethyl, 2-hydroxypropyl, 2-aminoethyl, 4-aminobutyl and 6-aminohexyl group.

The cycloalkyl group in $R^{11}$, $R^{12}$, $R^{13}$, $R^{14}$, $R^{15}$, $R^{16}$, $R^{17}$, $R^{18}$, $R^{19}$ and $R^{20}$ preferably has about 5 to 10 carbon atoms. Specific examples of the cycloalkyl group which may be substituted with at least one group selected from a hydroxyl group, an amino group which may be substituted with a C1-C4 alkyl group and a C1-C6 alkoxy group include a cyclopentyl, cyclohexyl, cycloheptyl and cyclooctyl group.

The aryl group in $R^{11}$, $R^{12}$, $R^{13}$, $R^{14}$, $R^{15}$, $R^{17}$, $R^{18}$, $R^{19}$ and $R^{20}$ preferably has about 6 to 10 carbon atoms. Specific examples of the aryl group which may be substituted with at least one group selected from a hydroxyl group, an amino group which may be substituted with a C1-C4 alkyl group and a C1-C6 alkoxy group include a phenyl and naphthyl group.

The alkoxy group in $R^{13}$, $R^{14}$ and $R^{15}$ preferably has about 1 to 6 carbon atoms and specific examples thereof include a methoxy, ethoxy, n-propoxy, isopropoxy, n-butoxy, tert-butoxy, n-pentyloxy and n-hexyloxy group.

The alkylene and alkenylene groups in W preferably have 2 to 6 carbon atoms. Specific examples of the alkylene group include an ethylene, trimethylene, tetramethylene, methylenedioxy and ethylene-1,2-dioxy group, and specific examples of the alkenylene group include an ethane-1,2-diyl, 1-propene-1,3-diyl and 2-butene-1,4-diyl group.

Specific examples of the amine compound include n-hexylamine, n-heptylamine, n-octylamine, n-nonylamine, n-decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptyamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecyamine, dicyclohexylmethylamine, tris[2-(2-methoxyethoxy)ethyl]amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skeleton as disclosed in JP 11-52575 A1 can be also used as the quencher.

In the point of forming patterns having higher resolution, the quaternary ammonium hydroxide is preferably used as the quencher.

When the basic compound is used as the quencher, the present resist composition preferably includes 0.01 to 1% by weight of the basic compound based on the total amount of the resin component and Salt (I).

The present resist composition can contain, if necessary, a small amount of various additives such as a sensitizer, a solution suppressing agent, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A resist film applied onto the substrate and then dried is subjected to exposure for patterning, then heat-treated to facilitate a deblocking reaction, and thereafter developed with an alkali developer. The alkali developer used may be any one of various alkaline aqueous solution used in the art. Generally, an aqueous solution of tetramethylammonium hydroxide or (2-hydroxyethyl)trimethylammonium hydroxide (commonly known as "choline") is often used.

It should be construed that embodiments disclosed here are examples in all aspects and not restrictive. It is intended that the scope of the present invention is determined not by the above descriptions but by appended Claims, and includes all variations of the equivalent meanings and ranges to the Claims.

The present invention will be described more specifically by Examples, which are not construed to limit the scope of the present invention. The "%" and "part(s)" used to represent the content of any component and the amount of any material to be used in the following Examples are on a weight basis unless otherwise specifically noted. The weight-average molecular weight of any material in the following Examples is a value found by gel permeation chromatography [HLC-8120GPC Type, Column (Total 3 Columns): TSKgel Multipore HXL-M manufactured by TOSOH CORPORATION, Solvent: tetrahydrofuran] using polystyrene as a standard reference material.

Structures of salts obtained were determined by NMR (EX-270 Type manufactured by JEOL LTD.) and mass spectrometry (Liquid Chromatography: 1100 Type manufactured by AGILENT TECHNOLOGIES LTD., Mass Spectrometry: LC/MSD Type or LC/MSD TOF Type manufactured by AGILENT TECHNOLOGIES LTD.).

REFERENCE EXAMPLE 1

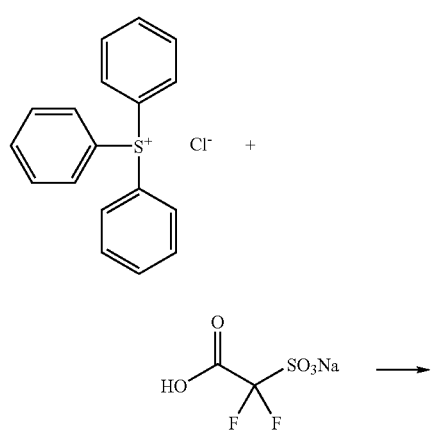

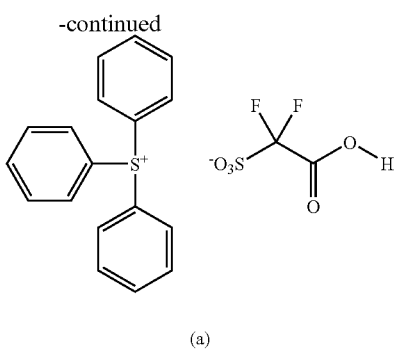

(a)

300.0 Parts of 18% aqueous sodium salt of difluorosulfoacetic acid solution was added to 573.7 parts of 14.2% aqueous triphenylsulfonium chloride solution and the resultant mixture was stirred at 25° C. for about 20 hours. The white precipitates were filtrated, washed with 100 parts of ion-exchanged water and dried to obtain 88.4 parts of the salt represented by the above-mentioned formula (a).

$^1$H-NMR (dimethylsulfoxide-$d_6$, Internal standard: tetramethylsilane): δ (ppm) 7.77-7.88 (m, 15H), 13.90 (br, 1H) MS (ESI(+) Spectrum): M$^+$ 263.2 ($C_{18}H_{15}S^+$=263.09) MS (ESI(−) Spectrum): M$^-$ 175.0 ($C_2HF_2O_5S^-$=174.95)

SALT SYNTHESIS EXAMPLE 1

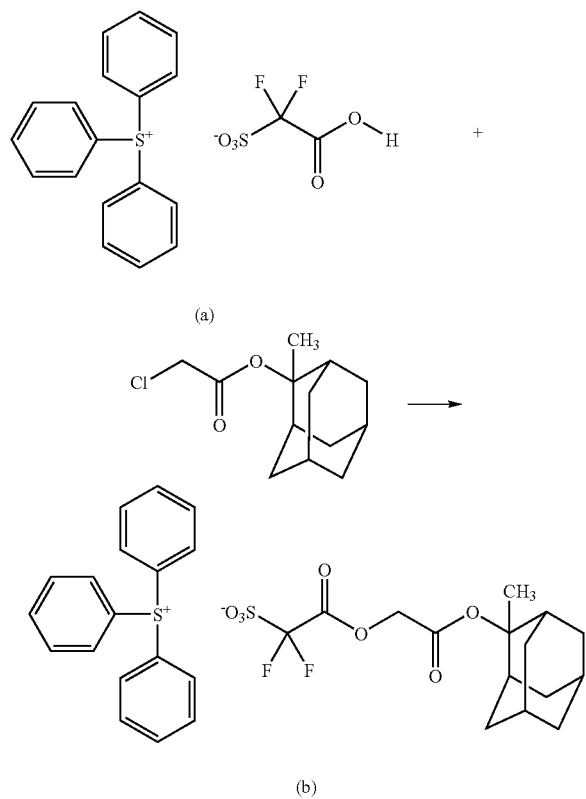

8.8 Parts of the salt represented by the above-mentioned formula (a) was dissolved in 70.2 parts of N,N-dimethylformamide. To the solution obtained, 2.8 parts of potassium carbonate and 0.8 part of potassium iodide were added, and the resulting mixture was stirred at 50° C. for about 1 hour. The mixture was cooled to 40° C. and a solution obtained by dissolving 4.9 parts of 2-methyl-2-adamantyl 2-chloroacetate in 10 parts of N,N-dimethylformamide was added dropwise thereto to stir at 40° C. for 44 hours. After the completion of the reaction, 98 parts of chloroform and 98 parts of ion-exchanged water were added to the reaction mixture. The resulting mixture was stirred and allowed to stand to separate into an organic layer and an aqueous layer. The aqueous layer was extracted twice with 98 parts of chloroform and the chloroform layers obtained were mixed with the organic layer. The resulting organic layer was repeated to wash with 98 parts of ion-exchanged water until the aqueous layer obtained was neutralized. The organic layer was concentrated to obtain the residue. 77 Parts of ethyl acetate was added to the residue to stir. The white solid precipitated was filtrated and dried to obtain 7.8 parts of the salt represented by the above-mentioned formula (b), which is called as B1.

$^1$H-NMR (dimethylsulfoxide-$d_6$, Internal standard: tetramethylsilane): δ (ppm) 1.48-1.99 (m, 15H), 2.19 (s, 2H), 4.80 (s, 2H), 7.74-7.89 (m, 15H) MS (ESI(+) Spectrum): M$^+$ 263.0 ($C_{18}H_{15}S^+$=263.09) MS (ESI(−) Spectrum): M$^-$ 381.0 ($C_{15}H_{19}F_2O_7S^-$=381.08)

SALT SYNTHESIS EXAMPLE 2

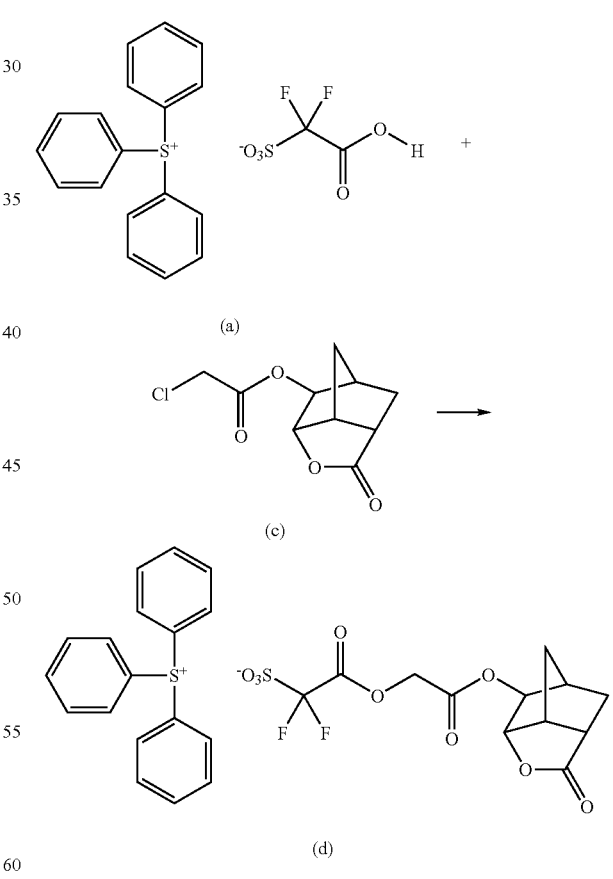

9.5 Parts of the salt represented by the above-mentioned formula (a) was dissolved in 47.6 parts of N,N-dimethylformamide. To the solution obtained, 3.0 parts of potassium carbonate and 0.9 part of potassium iodide were added, and the resulting mixture was stirred at 50° C. for about 1 hour. The mixture was cooled to 40° C. and a solution obtained by dissolving 5.0 parts of the compound represented by the above-mentioned formula (c) in 40 parts of N,N-dimethylformamide was added dropwise thereto to stir at 40° C. for 23 hours. After the completion of the reaction, 106 parts of chloroform and 106 parts of ion-exchanged water were added to the reaction mixture. The resulting mixture was stirred and allowed to stand to separate into an organic layer and an aqueous layer. The aqueous layer was extracted twice with 106 parts of chloroform and the chloroform layers obtained were mixed with the organic layer. The resulting organic layer was repeated to wash with 106 parts of ion-exchanged water until the aqueous layer obtained was neutralized. 3.5 Parts of activated carbon was added to the organic layer to stir. The mixture was filtered and the filtrate was concentrated to obtain the residue. 38 parts of ethyl acetate was added to the residue to stir. After standing, the supernatant liquid was removed by decantation. To the residue, 38 parts of tert-butyl methyl ether was added and stirred. After standing, the supernatant liquid was removed by decantation. The residue was dissolved in chloroform and the solution obtained was concentrated to obtain 4.3 parts of the salt represented by the above-mentioned formula (d) in a form of orange oil, which is called as B2.

$^1$H-NMR (dimethylsulfoxide-d$_6$, Internal standard: tetramethylsilane): δ (ppm) 1.59 (t, 2H, J=11.5 Hz), 1.87-2.06 (m, 2H), 2.41-2.53 (m, 2H), 3.17 (t, 1H, J=4.6 Hz), 4.53-4.56 (m, 2H), 4.89 (s, 2H), 7.74-7.89 (m, 15H) MS (ESI(+) Spectrum): M$^+$ 263.0 (C$_{18}$H$_{15}$S$^+$=263.09) MS (ESI(−) Spectrum): M$^-$ 369.0 (C$_{12}$H$_{11}$F$_2$O$_9$S$^-$=369.01)

SALT SYNTHESIS EXAMPLE 3 mamide. To the solution obtained, 2.9 parts of potassium carbonate and 0.9 part of potassium iodide were added, and the resulting mixture was stirred at 50° C. for about 1 hour. The mixture was cooled to 40° C. and a solution obtained by dissolving 5.0 parts of 4-oxo-1-adamantyl 2-chloroacetate in 10 parts of N,N-dimethylformamide was added dropwise thereto to stir at 40° C. for 32 hours. After the completion of the reaction, 73 parts of chloroform and 73 parts of ion-exchanged water were added to the reaction mixture. The resulting mixture was stirred and allowed to stand to separate into an organic layer and an aqueous layer. The aqueous layer was extracted twice with 73 parts of chloroform and the chloroform layers obtained were mixed with the organic layer. The resulting organic layer was repeated to wash with 73 parts of ion-exchanged water until the aqueous layer obtained was neutralized. 3.1 Parts of activated carbon was added to the organic layer to stir. The mixture was filtered and the filtrate was concentrated to obtain the residue. 84 parts of ethyl acetate was added to the residue to stir, and the mixture was filtered. The filtrate obtained was concentrated and 60 parts of tert-butyl methyl ether was added to the residue obtained. The precipitate was filtrated to obtain 4.9 parts of the salt represented by the above-mentioned formula (e) in a form of pale yellow solid, which is called as B3.

$^1$H-NMR (dimethylsulfoxide-d$_6$, Internal standard: tetramethylsilane): δ (ppm) 1.81 (d, 2H, J=12.7 Hz), 1.97 (d, 2H, J=12.2 Hz), 2.23-2.35 (m, 7H), 2.50 (s, 2H), 4.77 (s, 2H), 7.74-7.89 (m, 15H) MS (ESI(+) Spectrum): M$^+$ 263.1 (C$_{18}$H$_{15}$S$^+$=263.09) MS (ESI(−) Spectrum): M$^-$ 381.1 (C$_{14}$H$_{15}$F$_2$O$_8$S$^-$=381.05)

COMPARATIVE SALT SYNTHESIS EXAMPLE 1

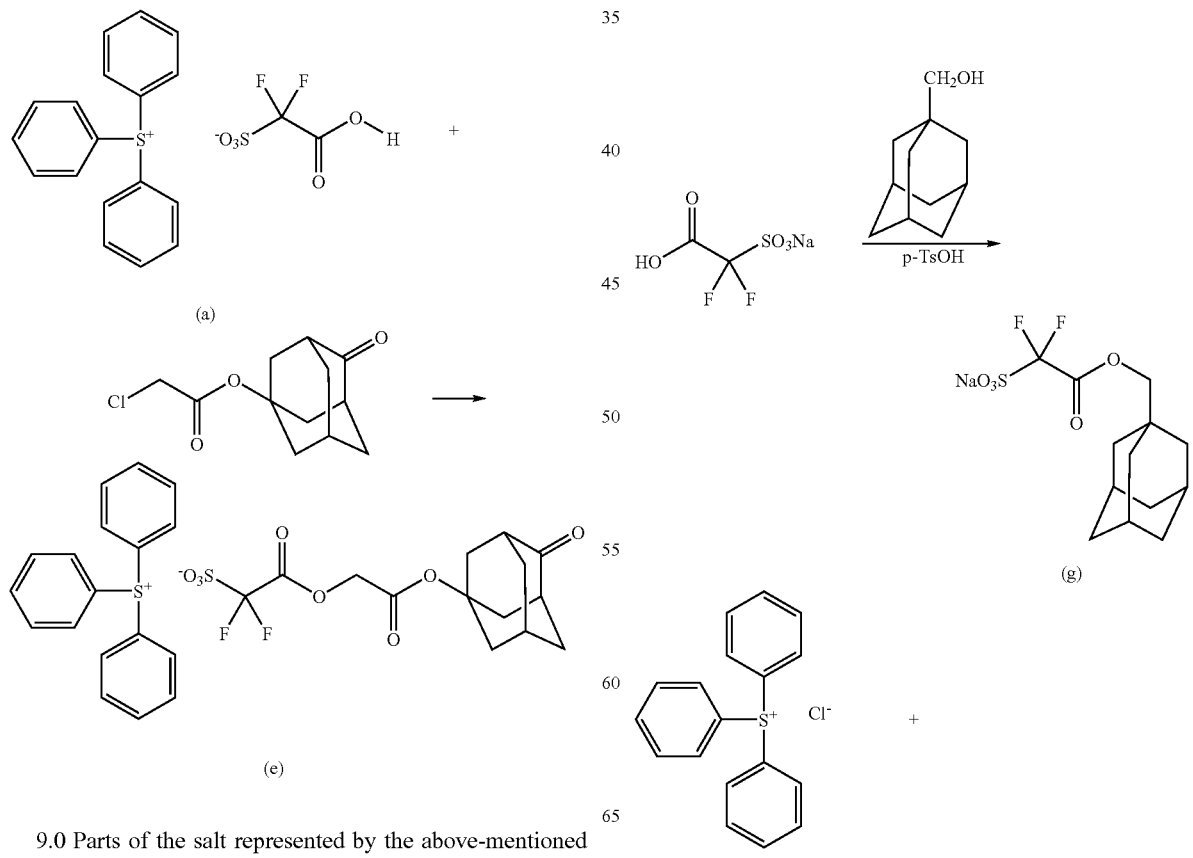

9.0 Parts of the salt represented by the above-mentioned formula (a) was dissolved in 45.2 parts of N,N-dimethylfor- -continued

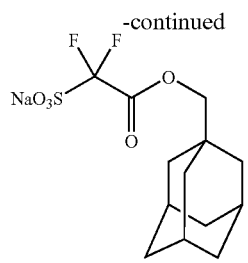

(g)

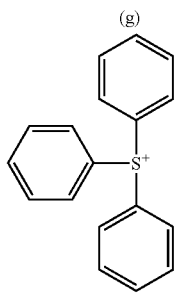

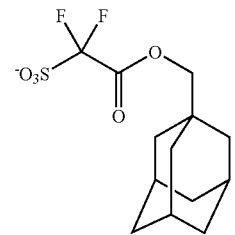

(f)

(1) 24.0 Parts of p-toluenesulfonic acid was added to a mixture of 39.4 Parts of sodium salt of difluorosulfoacetic acid (purity: 63.5%), 21.0 parts of 1-adamantanemethanol and 200 parts of dichloroethane, and the resultant mixture was heated and refluxed for 7 hours. The mixture was concentrated to remove dichloroethane and 250 parts of tert-butyl methyl ether was added to the residue obtained. The mixture obtained was stirred and filtrated to obtain the solid. To the solid, 250 parts of acetonitrile was added and the resultant mixture was stirred and filtrated. The filtrates obtained were mixed and the solution obtained was concentrated to obtain 32.8 parts of the salt represented by the above-mentioned formula (g).

(2) 32.8 Parts of the salt obtained in the above-mentioned (1) was dissolved in 100 parts of ion-exchanged water. To the solution obtained, a mixture of 28.3 parts of triphenylsulfonium chloride and 140 parts of methanol was added to stir for 15 hours. The resultant mixture was concentrated. The residue obtained was extracted twice with 200 parts of chloroform. The organic layers obtained were washed with ion-exchanged water and concentrated. To the concentrated liquid, 300 parts of tert-butyl methyl ether was added and stirred. The resultant mixture was filtrated and the solid obtained was dried to obtain 39.7 parts of the salt represented by the above-mentioned formula (f) in the form of white solid, which is called as C1.

$^1$H-NMR (dimethylsulfoxide-$d_6$, Internal standard: tetramethylsilane): δ (ppm) 1.52 (d, 6H), 1.63 (dd, 6H), 1.93 (s, 3H), 3.81 (s, 2H), 7.76-7.90 (m, 15H) MS (ESI(+) Spectrum): $M^+$ 263.2 ($C_{18}H_{15}S^+$=263.09) MS (ESI(−) Spectrum): $M^-$ 323.0 ($C_{13}H_{17}F_2O_5S^-$=323.08)

RESIN SYNTHESIS EXAMPLE 1

2-Ethyl-2-adamantyl methacrylate, 3-hydroxy-1-adamantyl methacrylate and α-methacryloyloxy-γ-butyrolactone were dissolved in 2 times amount of methyl isobutyl ketone as much as the amount of all monomers to be used (monomer molar ratio; 2-ethyl-2-adamantyl methacrylate:3-hydroxy-1-adamantyl methacrylate:α-methacryloyloxy-γ-butyrolactone=5:2.5:2.5). To the solution, 2,2'-azobisisobutyronitrile was added as an initiator in a ratio of 2 mol % based on all monomer molar amount, and the resultant mixture was heated at 80° C. for about 8 hours. The reaction solution was poured into large amount of heptane to cause precipitation. The precipitate was isolated and washed twice with large amount of heptane for purification. As a result, copolymer having a weight-average molecular weight of about 9,200 was obtained. This copolymer had the following structural units. This is called as resin A1.

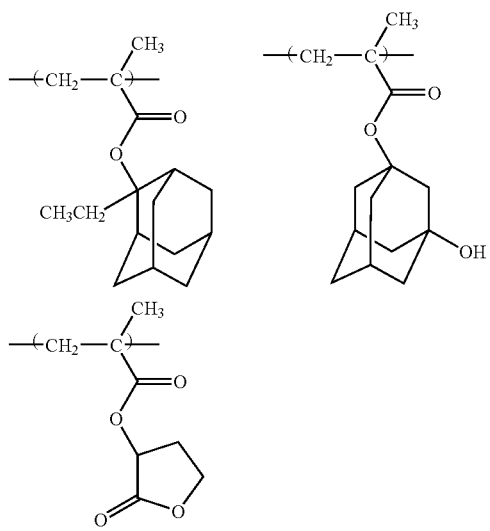

EXAMPLES 1 TO 3 AND COMPARATIVE EXAMPLE 1

<Resin>

Resin A1

<Acid Generator>

Acid generator B1:

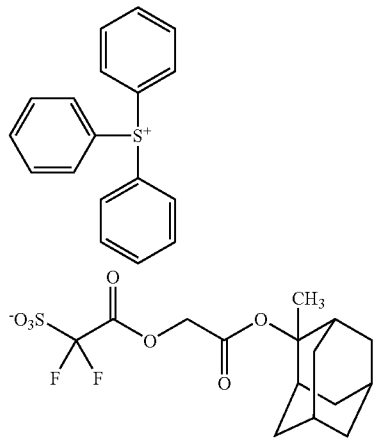

Acid Generator B2:

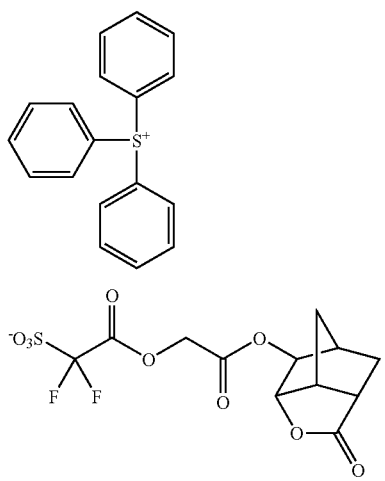

Acid Generator B3:

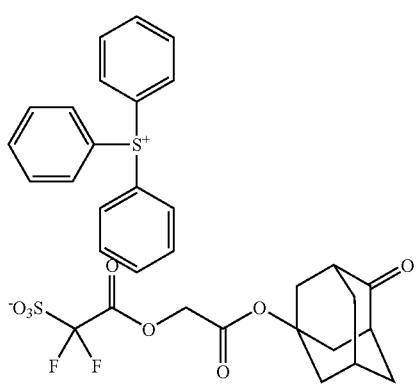

Acid Generator C1:

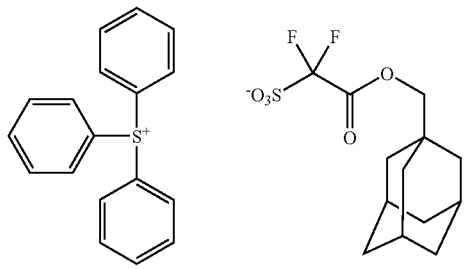

<Quencher>

Quencher Q1: 2,6-diisopropylaniline

<Solvent>

| Solvent Y1: | propylene glycol monomethyl ether acetate | 51.5 parts |
|---|---|---|
| | 2-heptanone | 35.0 parts |
| | γ-butyrolactone | 3.5 parts |

The following components were mixed to give a solution, and the solution was further filtrated through a fluorine resin filter having a pore diameter of 0.2 μm, to prepare resist liquid.

Resin (kind and amount are described in Table 1)
Acid generator (kind and amount are described in Table 1)
Quencher (kind and amount are described in Table 1)
Solvent (kind and amount are described in Table 1)

TABLE 1

| Ex. No. | Resin (kind/amount (part)) | Acid generator (kind/amount (part)) | Quencher (kind/amount (part)) | Solvent |
|---|---|---|---|---|
| Ex. 1 | A1/10 | B1/0.2857 | Q1/0.0325 | Y1 |
| Ex. 2 | A1/10 | B2/0.2804 | Q1/0.0325 | Y1 |
| Ex. 3 | A1/10 | B3/0.2857 | Q1/0.0325 | Y1 |
| Comp. Ex. 1 | A1/10 | C1/0.26 | Q1/0.0325 | Y1 |

Silicon wafers were each coated with "ARC-95", which is an organic anti-reflective coating composition available from Nissan Chemical Industries, Ltd., and then baked under the conditions of 205° C. and 60 seconds, to form a 295 Å-thick organic anti-reflective coating. Each of the resist liquids prepared as above was spin-coated over the anti-reflective coating so that the thickness of the resulting film became 0.25 μm after drying. After application of each of the resist liquids, the silicon wafers thus coated with the respective resist liquids were each prebaked on a proximity hotplate at a temperature of 125° C. for 60 seconds. Using an ArF excimer stepper ("FPA-5000AS3" manufactured by CANON INC., NA=0.75, ⅔ Annular), each wafer on which the respective resist film had been thus formed was exposed to a line and space pattern, while changing stepwise the exposure quantity.

After the exposure, each wafer was subjected to post-exposure baking on a hotplate at a temperature of 125° C. for 60 seconds and then to development for 15 seconds with an aqueous solution of 2.38% tetramethylammonium hydroxide.

Each of line and space pattern developed on the organic anti-reflective coating substrate after the development was observed with a scanning electron microscope and Each of width of line was measured, and the results of which are shown in Table 2.

Effective Sensitivity (ES): It is expressed as the amount of exposure that the width of line of 100 nm line and space pattern became just 100 nm.

Resolution: It is expressed as the minimum size of space pattern which gave the space pattern split by the line pattern at the exposure amount of the effective sensitivity.

Exposure margin: It is expressed as the value calculated by dividing the difference between 115 nm and 85 nm (=30 nm) by the difference between the max and minimum value of the amount of exposure that the width of line became 115 to 85 nm. The smaller the value is, the more excellent the exposure margin is.

TABLE 2

| Ex. No. | ES (mJ/cm$^2$) | Resolution (nm) | Exposure margin (nm/mJ) |
|---|---|---|---|
| Ex. 1 | 27 | 90 | 6.1 |
| Ex. 2 | 37 | 85-90 | 4.1 |
| Ex. 3 | 32 | 85 | 3.9 |
| Comp. Ex. 1 | 27 | 90 | 6.9 |

The salt represented by the formula (I) is suitably used for an acid generator capable of providing a chemically amplified positive resist composition giving patterns having good resolution and excellent exposure margin, and the present resist composition is especially suitable for ArF excimer laser lithography, KrF excimer laser lithography and ArF immersion lithography.

What is claimed is:

1. A salt represented by the formula (I):

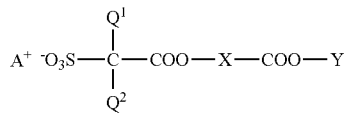

wherein X represents a C1-C12 divalent linear or branched chain hydrocarbon group, Y represents a C1-C30 hydrocarbon group which may be substituted with at least one substituent, and at least one —CH$_2$— in the C1-C30 hydrocarbon group may be substituted with —O— or —CO—, Q$^1$ and Q$^2$ each independently represent a fluorine atom or a C1-C6 perfluoroalkyl group, and A$^+$ represents an organic counter ion.

2. The salt according to claim 1, wherein Q$^1$ and Q$^2$ each independently represent a fluorine atom or a trifluoromethyl group.

3. The salt according to claim 1, wherein the organic counter ion is at least one cation selected from a cation represented by the formula (IIa):

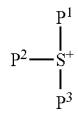

wherein P$^1$, P$^2$ and P$^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

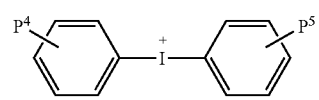

wherein P$^4$ and P$^5$ each independently represent a hydrogen atom, a hydroxyl group, a C1-C12 alkyl group or a C1-C12 alkoxy group, a cation represented by the formula (IIc):

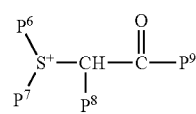

wherein P$^6$ and P$^7$ each independently represent a C1-C12 alkyl group or a C3-C12 cycloalkyl group, or P$^6$ and P$^7$ are bonded to form a C3-C12 divalent acyclic hydrocarbon group which forms a ring together with the adjacent S$^+$, and at least one —CH$_2$— in the divalent acyclic hydrocarbon group may be substituted with —CO—, —O— or —S—, P$^8$ represents a hydrogen atom, P$^9$ represents a C1-C12 alkyl group, a C3-C12 cycloalkyl group or an aromatic group which may be substituted, or P$^8$ and P$^9$ are bonded to form a divalent acyclic hydrocarbon group which forms a 2-oxocycloalkyl group together with the adjacent —CHCO—, and at least one —CH$_2$— in the divalent acyclic hydrocarbon group may be substituted with —CO—, —O— or —S—, and a cation represented by the formula (IId):

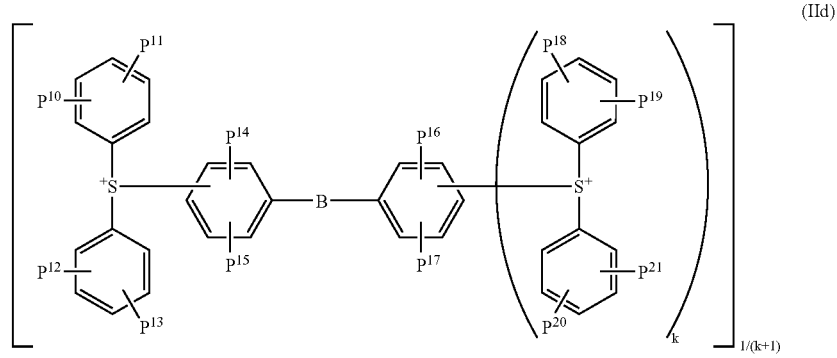

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1.

4. The salt according to claim 1, wherein the organic counter ion is a cation represented by the formula (IIIa), (IIIb) or (IIIc):

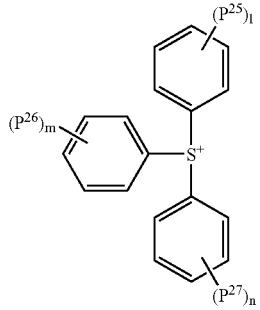
(IIIa)

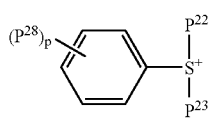
(IIIb)

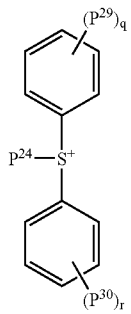
(IIIc)

wherein $P^{22}$, $P^{23}$ and $P^{24}$ each independently represent a C1-C20 alkyl group or a C3-C30 cyclic hydrocarbon group except a phenyl group, wherein at least one hydrogen atom in the C1-C20 alkyl group may be substituted with a hydroxyl group, a C1-C12 alkoxy group or a C3-C12 cyclic hydrocarbon group and wherein at least one hydrogen atom in the C3-C30 cyclic hydrocarbon group may be substituted with a hydroxyl group, a C1-C12 alkyl group or a C1-C12 alkoxy group, and $P^{25}$, $P^{26}$, $P^{27}$, $P^{28}$, $P^{29}$ and $P^{30}$ each independently represent a hydroxyl group, a C1-C12 alkyl group, a C1-C12 alkoxy group or a C3-C12 cyclic hydrocarbon group, and l, m, n, p, q and r each independently represent an integer of 0 to 5.

5. The salt according to claim 1, wherein the organic counter ion is a cation represented by the formula (IIIa):

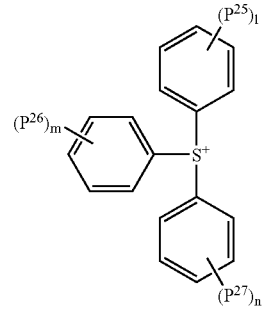
(IIIa)

wherein $P^{25}$, $P^{26}$, $P^{27}$, l, m and n are the same meanings as defined in claim 4.

6. The salt according to claim 1, wherein Y represents a C1-C20 hydrocarbon group which may be substituted with at least one selected from a C1-C6 alkoxy group, a C1-C4 perfluoroalkyl group, a C1-C6 hydroxyalkyl group, a hydroxyl group and a cyano group, and at least one —CH$_2$— except terminal —CH$_2$— in the C1-C20 hydrocarbon group may be substituted with —O— or —CO—.

7. The salt according to claim 1, wherein the C1-C12 divalent linear or branched chain hydrocarbon group is a following group.

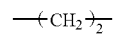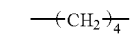

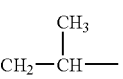

8. The salt according to claim 1, wherein the C1-C12 divalent linear or branched chain hydrocarbon group is a methylene, ethylene, trimethylene, tetramethylene, hexamethylene, octamethylene or dodecamethylene group.

9. The salt according to claim 1, wherein the salt represented by the formula (I) is one represented by the formula (IVa), (IVb) or (IVc):

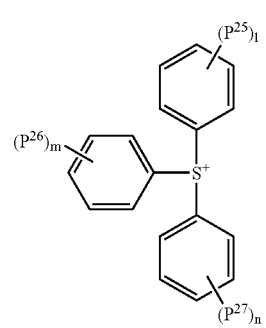
(IVa)

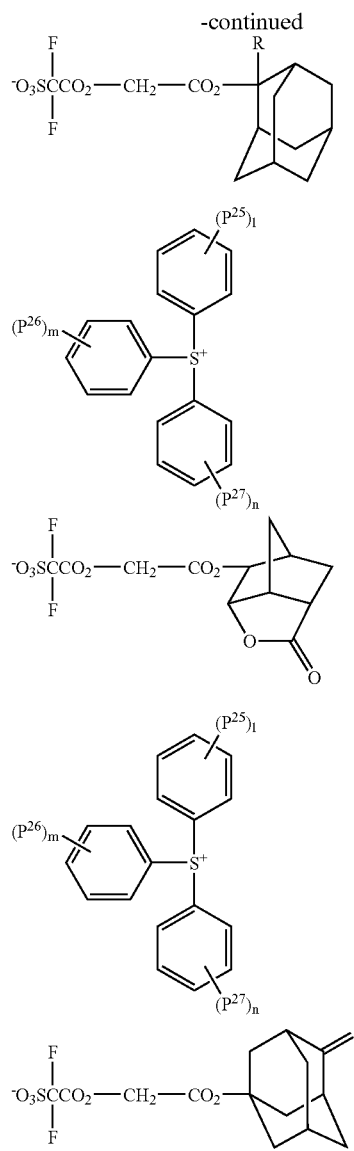

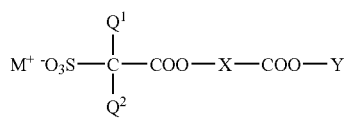

wherein $P^{25}$, $P^{26}$, $P^{27}$, l, m and n are the same meanings as defined in claim 4 and R represents a C1-C6 alkyl group.

10. A salt represented by the formula (V):

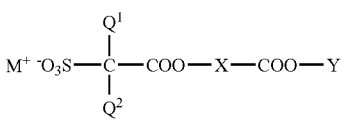

wherein X represents a C1-C12 divalent linear or branched chain hydrocarbon group, Y represents a C1-C30 hydrocarbon group which may be substituted with at least one substituent, and at least one —$CH_2$— in the C1-C30 hydrocarbon group may be substituted with —O— or —CO—, $Q^1$ and $Q^2$ each independently represent a fluorine atom or a C1-C6 perfluoroalkyl group, and M represents Li, Na, K or Ag.

11. A process for production of a salt represented by the formula (V):

wherein X represents a C1-C12 divalent linear or branched chain hydrocarbon group, Y represents a C1-C30 hydrocarbon group which may be substituted with at least one substituent, and at least one —$CH_2$— in the C1-C30 hydrocarbon group may be substituted with —O— or —CO—, $Q^1$ and $Q^2$ each independently represent a fluorine atom or a C1-C6 perfluoroalkyl group, and M represents Li, Na, K or Ag, which comprises reacting a compound represented by the formula (VI):

$$Z\text{-}X\text{—}COO\text{—}Y \qquad (VI)$$

wherein X and Y are the same as defined above, and Z represents Cl, Br or I, with a compound represented by the formula (VII):

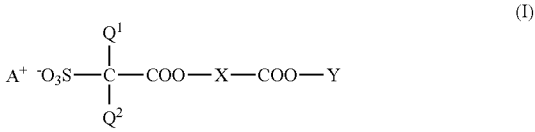

wherein $Q^1$, $Q^2$ and M are the same as defined above.

12. A process for production of a salt represented by the formula (I):

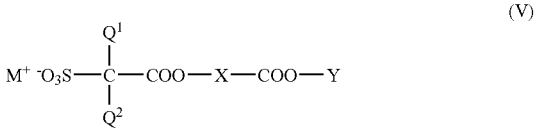

wherein X represents a C1-C12 divalent linear or branched chain hydrocarbon group, Y represents a C1-C30 hydrocarbon group which may be substituted with at least one substituent, and at least one —$CH_2$— in the C1-C30 hydrocarbon group may be substituted with —O— or —CO—, $Q^1$ and $Q^2$ each independently represent a fluorine atom or a C1-C6 perfluoroalkyl group, and $A^+$ represents an organic counter ion, which comprises reacting a salt represented by the formula (V):

wherein X, Y, $Q^1$ and $Q^2$ are the same as defined above and M represents Li, Na, K or Ag, with a compound represented by the formula (VIII):

$$A^+\text{-}L \qquad (VIII)$$

wherein $A^+$ is as defined above and L represents F, Cl, Br, I, $BF_4$, $AsF_6$, $SbF_6$, $PF_6$ or $ClO_4$.

13. A process for production of a salt represented by the formula (I):

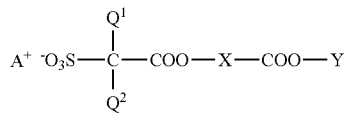

wherein X represents a C1-C12 divalent linear or branched chain hydrocarbon group, Y represents a C1-C30 hydrocarbon group which may be substituted with at least one substituent, and at least one —$CH_2$— in the C1-C30 hydrocarbon group may be substituted with —O— or —CO—, $Q^1$ and $Q^2$ each independently represent a fluorine atom or a C1-C6 perfluoroalkyl group, and $A^+$ represents an organic counter ion, which comprises reacting a salt represented by the formula (IX):

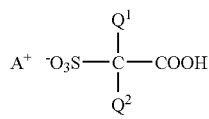

wherein $Q^1$, $Q^2$ and $A^+$ are the same as defined above, with a compound represented by the formula (VI):

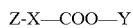

Z-X—COO—Y    (VI)

wherein X and Y are the same as defined above, and Z represents Cl, Br or I.

14. A chemically amplified positive resist composition comprising a salt represented by the formula (I):

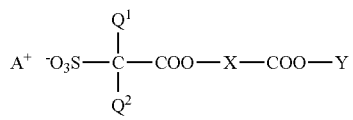

wherein X represents a C1-C12 divalent linear or branched chain hydrocarbon group, Y represents a C1-C30 hydrocarbon group which may be substituted with at least one substituent, and at least one —$CH_2$— in the C1-C30 hydrocarbon group may be substituted with —O— or —CO—, $Q^1$ and $Q^2$ each independently represent a fluorine atom or a C1-C6 perfluoroalkyl group, and $A^+$ represents an organic counter ion, and a resin which contains a structural unit which has an acid-labile group and which itself is insoluble or poorly soluble in an aqueous alkali solution but becomes soluble in an aqueous alkali solution by the action of an acid.

15. The chemically amplified positive resist composition according to claim 14, wherein $Q^1$ and $Q^2$ each independently represent a fluorine atom or a trifluoromethyl group.

16. The chemically amplified positive resist composition according to claim 14, wherein the organic counter ion is at least one cation selected from a cation represented by the formula (IIa):

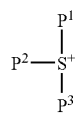

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

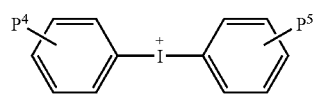

wherein $P^4$ and $P^5$ each independently represent a hydrogen atom, a hydroxyl group, a C1-C12 alkyl group or a C1-C12 alkoxy group, a cation represented by the formula (IIc):

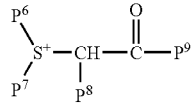

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —$CH_2$— in the divalent acyclic hydrocarbon group may be substituted with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ are bonded to form a divalent acyclic hydrocarbon group which forms a 2-oxocycloalkyl group together with the adjacent —CHCO—, and at least one —$CH_2$— in the divalent acyclic hydrocarbon group may be substituted with —CO—, —O— or —S—, and a cation represented by the formula (IId):

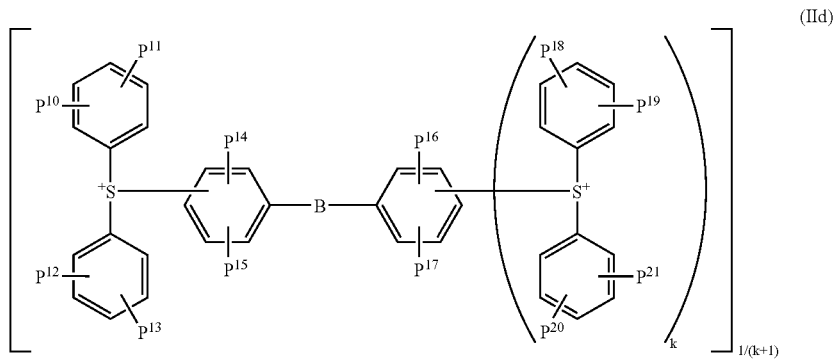

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1.

17. The chemically amplified positive resist composition according to claim 14, wherein the organic counter ion is a cation represented by the formula (IIIa), (IIIb) or (IIIc):

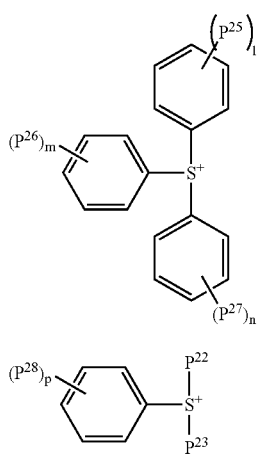

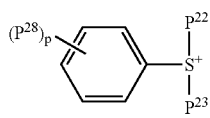

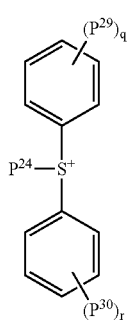

wherein $P^{22}$, $P^{23}$ and $P^{24}$ each independently represent a C1-C20 alkyl group or a C3-C30 cyclic hydrocarbon group except a phenyl group, wherein at least one hydrogen atom in the C1-C20 alkyl group may be substituted with a hydroxyl group, a C1-C12 alkoxy group or a C3-C12 cyclic hydrocarbon group and wherein at least one hydrogen atom in the C3-C30 cyclic hydrocarbon group may be substituted with a hydroxyl group, a C1-C12 alkyl group or a C1-C12 alkoxy group; and $P^{25}$, $P^{26}$, $P^{27}$, $P^{28}$, $P^{29}$ and $P^{30}$ each independently represent a hydroxyl group, a C1-C12 alkyl group, a C1-C12 alkoxy group or a C3-C12 cyclic hydrocarbon group, and l, m, n, p, q and r each independently represent an integer of 0 to 5.

18. The chemically amplified positive resist composition according to claim 14, wherein the organic counter ion is a cation represented by the formula (IIIa):

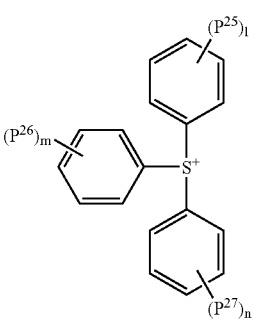

wherein and $P^{25}$, $P^{26}$, $P^{27}$, l, m and n are the same meanings as defined in claim 17.

19. The chemically amplified positive resist composition according to claim 14, wherein the salt represented by the formula (I) is one represented by the formula (IVa), (IVb) or (IVc):

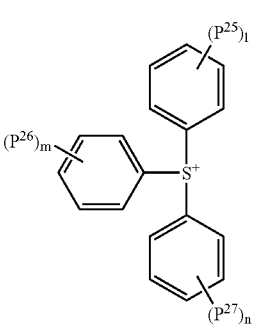

-continued

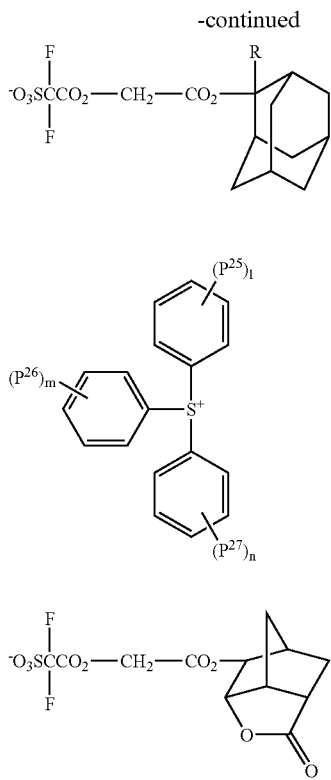

(IVb)

-continued

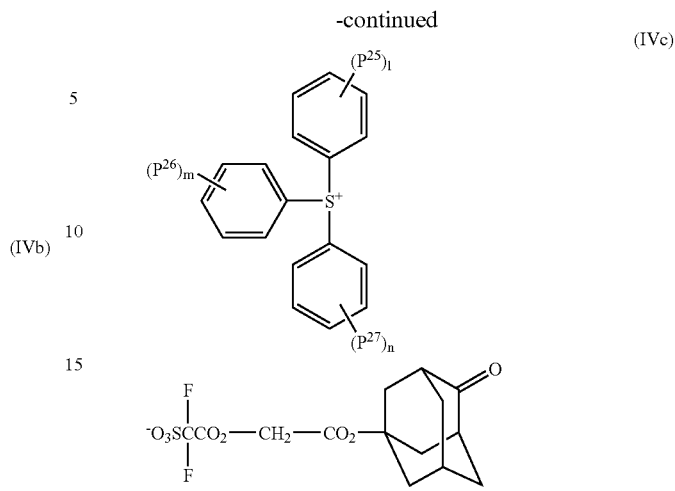

(IVc)

wherein $P^{25}$, $P^{26}$, $P^{27}$, l, m and n are the same meanings as defined in claim 17 and R represents a C1-C6 alkyl group.

20. The chemically amplified positive resist composition according to claim 14, the resin contains a structural unit derived from a monomer having a bulky and acid-labile group.

21. The chemically amplified positive resist composition according to claim 14, wherein the chemically amplified positive resist composition further comprises a basic compound.

* * * * *